(12) United States Patent
Burdick et al.

(10) Patent No.: US 10,737,095 B2
(45) Date of Patent: *Aug. 11, 2020

(54) NEUROSTIMULATOR

(71) Applicants: California Institute of Technology, Pasadena, CA (US); University of Louisville Research Foundation, Inc., Louisville, KY (US); The Regents of the University of California, Oakland, CA (US)

(72) Inventors: Joel W. Burdick, Pasadena, CA (US); Yu-Chong Tai, Pasadena, CA (US); John F. Naber, Goshen, KY (US); Robert S. Keynton, Louisville, KY (US); Victor Reggie Edgerton, Los Angeles, CA (US); Roland R Roy, Playa Vista, CA (US); Yury Gerasimenko, Los Angeles, CA (US); Susan J. Harkema, Louisville, KY (US); Jonathan Hodes, Louisville, KY (US); Claudia A. Angeli, Louisville, KY (US); Mandheerej S. Nandra, Pasadena, CA (US); Thomas Anthony Desautels, Pasadena, CA (US); Steven L. Upchurch, Louisville, KY (US); Douglas J. Jackson, New Albany, IN (US); Nicholas A. Terrafranca, Jr., Laguna Niguel, CA (US); Yangsheng Chen, Louisville, KY (US)

(73) Assignee: Californina Institute of Technology, Pasadena, CA (US)

( * ) Notice: Subject to any disclaimer, the term of this patent is extended or adjusted under 35 U.S.C. 154(b) by 50 days.

This patent is subject to a terminal disclaimer.

(21) Appl. No.: 15/940,473

(22) Filed: Mar. 29, 2018

(65) Prior Publication Data

US 2018/0229038 A1    Aug. 16, 2018

Related U.S. Application Data

(63) Continuation of application No. 15/199,580, filed on Jun. 30, 2016, now Pat. No. 9,931,508, which is a
(Continued)

(51) Int. Cl.
  *A61N 1/36*  (2006.01)
  *A61N 1/05*  (2006.01)
  (Continued)

(52) U.S. Cl.
  CPC .......... *A61N 1/36103* (2013.01); *A61B 5/407* (2013.01); *A61B 5/4076* (2013.01);
  (Continued)

(58) Field of Classification Search
  USPC .......................................................... 607/49
  See application file for complete search history.

(56) References Cited

U.S. PATENT DOCUMENTS

| 3,543,761 A | 12/1970 | Bradley |
| 3,662,758 A | 5/1972 | Glover |

(Continued)

FOREIGN PATENT DOCUMENTS

| EP | 2688642 | 1/2014 |
| JP | 2002-200178 | 7/2002 |

(Continued)

OTHER PUBLICATIONS

Examination Report for Australian Patent Application No. 2017202237 dated Apr. 6, 2018.
(Continued)

*Primary Examiner* — Nicole F Lavert
(74) *Attorney, Agent, or Firm* — K&L Gates LLC

(57) ABSTRACT

Neurostimulator devices are described. An example neurostimulator device includes a stimulation assembly connectable to a plurality of electrodes, wherein the plurality of electrodes are configured to stimulate a spinal cord. The neurostimulator device also includes an interface and at least one processor configured to modify at least one complex stimulation pattern deliverable by the plurality of electrodes by integrating data from the interface and performing a machine learning algorithm on the at least one complex stimulation pattern.

20 Claims, 19 Drawing Sheets

Related U.S. Application Data continuation of application No. 14/007,262, filed as application No. PCT/US2012/030624 on Mar. 26, 2012, now Pat. No. 9,409,023.

(60) Provisional application No. 61/467,107, filed on Mar. 24, 2011.

(51) Int. Cl.
*A61B 5/00* (2006.01)
*A61B 5/0492* (2006.01)
*A61B 5/11* (2006.01)

(52) U.S. Cl.
CPC .......... *A61B 5/4836* (2013.01); *A61N 1/0551* (2013.01); *A61N 1/0553* (2013.01); *A61N 1/36003* (2013.01); *A61N 1/36007* (2013.01); *A61N 1/3611* (2013.01); *A61N 1/36067* (2013.01); *A61N 1/36082* (2013.01); *A61N 1/36107* (2013.01); *A61N 1/36114* (2013.01); *A61N 1/36125* (2013.01); *A61N 1/36139* (2013.01); *A61B 5/0492* (2013.01); *A61B 5/1106* (2013.01); *A61B 2505/09* (2013.01)

(56) References Cited

U.S. PATENT DOCUMENTS

| | | |
|---|---|---|
| 3,724,467 A | 4/1973 | Avery et al. |
| 4,044,774 A | 8/1977 | Corbin et al. |
| 4,102,344 A | 6/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,414,986 A | 11/1983 | Dickhudt et al. |
| 4,538,624 A | 9/1985 | Tarjan |
| 4,549,556 A | 10/1985 | Tajan et al. |
| 4,800,898 A | 1/1989 | Hess et al. |
| 4,934,368 A | 6/1990 | Lynch |
| 5,002,053 A | 3/1991 | Garcia-Rill et al. |
| 5,031,618 A | 7/1991 | Mullett |
| 5,081,989 A | 1/1992 | Graupe |
| 5,121,754 A | 6/1992 | Mullett |
| 5,344,439 A | 9/1994 | Otten |
| 5,354,320 A | 10/1994 | Schaldach |
| 5,374,285 A | 12/1994 | Vaiani et al. |
| 5,417,719 A | 5/1995 | Hull et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,470,213 B1 | 10/2002 | Alley |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen |
| 6,871,099 B1 | 3/2005 | Whitehurst et al. |
| 6,892,098 B2 | 5/2005 | Ayal |
| 6,895,280 B2 | 5/2005 | Meadows |
| 6,895,283 B2 | 5/2005 | Erickson et al. |
| 6,937,891 B2 | 8/2005 | Leinders |
| 6,950,706 B2 | 9/2005 | Rodriguez |
| 6,975,907 B2 | 12/2005 | Zanakis |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng |
| 7,127,287 B2 | 10/2006 | Duncan |
| 7,127,296 B2 | 10/2006 | Bradley |
| 7,127,297 B2 | 10/2006 | Law et al. |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen |
| 7,239,920 B1 | 7/2007 | Thacker et al. |
| 7,251,529 B2 | 7/2007 | Greenwood-Van |
| 7,252,090 B2 | 8/2007 | Goetz |
| 7,313,440 B2 | 12/2007 | Miesel et al. |
| 7,330,760 B2 | 2/2008 | Heruth et al. |
| 7,337,005 B2 | 2/2008 | Kim |
| 7,377,006 B2 | 2/2008 | Kim |
| 7,340,298 B1 | 3/2008 | Barbut |
| 7,415,309 B2 | 8/2008 | McIntyre |
| 7,463,927 B1* | 12/2008 | Chaouat ............ A61N 1/36071 607/46 |
| 7,463,928 B2 | 12/2008 | Lee |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen |
| 7,660,636 B2 | 2/2010 | Castel et al. |
| 7,697,995 B2 | 4/2010 | Cross et al. |
| 7,729,781 B2 | 6/2010 | Swoyer et al. |
| 7,734,340 B2 | 6/2010 | De Ridder |
| 7,734,351 B2 | 6/2010 | Testerman |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,890,182 B2 | 2/2011 | Parramon et al. |
| 7,949,395 B2 | 5/2011 | Kuzma |
| 7,949,403 B2 | 5/2011 | Palermo |
| 7,987,000 B2 | 7/2011 | Moffitt et al. |
| 7,991,465 B2 | 8/2011 | Bartle et al. |
| 8,019,427 B2 | 9/2011 | Moffitt |
| 8,050,773 B2 | 11/2011 | Zhu |
| 8,108,052 B2 | 1/2012 | Boling |
| 8,131,358 B2 | 3/2012 | Moffitt |
| 8,155,750 B2 | 4/2012 | Jaax |
| 8,170,660 B2 | 5/2012 | Dacey |
| 8,190,262 B2 | 5/2012 | Gerber |
| 8,195,304 B2 | 6/2012 | Strother et al. |
| 8,239,038 B2 | 8/2012 | Wolf |
| 8,260,436 B2 | 9/2012 | Gerber et al. |
| 8,311,644 B2 | 11/2012 | Moffitt |
| 8,332,029 B2 | 12/2012 | Glukhovsky et al. |
| 8,346,366 B2 | 1/2013 | Arle |

(56) References Cited

U.S. PATENT DOCUMENTS

| | | |
|---|---|---|
| 8,352,036 B2 | 1/2013 | Dimarco |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishmamur |
| 8,805,542 B2 | 8/2014 | Tai |
| 9,409,023 B2 | 8/2016 | Burdick et al. |
| 2002/0055779 A1 | 5/2002 | Andrews |
| 2002/0111661 A1 | 8/2002 | Cross et al. |
| 2003/0032992 A1 | 2/2003 | Thacker |
| 2003/0078633 A1 | 4/2003 | Firlik et al. |
| 2004/0044380 A1 | 3/2004 | Buringa |
| 2004/0122483 A1 | 6/2004 | Nathan et al. |
| 2004/0133248 A1 | 7/2004 | Frei et al. |
| 2004/0138518 A1 | 7/2004 | Rise et al. |
| 2004/0172097 A1 | 9/2004 | Brodard et al. |
| 2004/0181263 A1 | 9/2004 | Blazer et al. |
| 2005/0004622 A1 | 1/2005 | Cullen et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0231186 A1 | 10/2005 | Barrera et al. |
| 2005/0246004 A1 | 11/2005 | Cameron et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0122678 A1 | 6/2006 | Olsen et al. |
| 2006/0142822 A1 | 6/2006 | Tulgar |
| 2006/0149337 A1 | 7/2006 | John |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2007/0016097 A1 | 1/2007 | Farquhar et al. |
| 2007/0049814 A1 | 3/2007 | Muccio |
| 2007/0060954 A1 | 3/2007 | Cameron et al. |
| 2007/0060980 A1 | 3/2007 | Strother et al. |
| 2007/0083240 A1 | 4/2007 | Peterson et al. |
| 2007/0156179 A1 | 7/2007 | S.E. |
| 2007/0179534 A1 | 8/2007 | Firlik et al. |
| 2007/0191709 A1 | 8/2007 | Swanson |
| 2007/0233204 A1 | 10/2007 | Lima |
| 2007/0265691 A1 | 11/2007 | Swanson |
| 2008/0009927 A1 | 1/2008 | Vilimis |
| 2008/0046049 A1 | 2/2008 | Skubitz et al. |
| 2008/0051851 A1 | 2/2008 | Lin |
| 2008/0103579 A1 | 5/2008 | Gerber |
| 2008/0140152 A1 | 6/2008 | Imran et al. |
| 2008/0140169 A1 | 6/2008 | Imran |
| 2008/0183224 A1 | 7/2008 | Barolat |
| 2008/0221653 A1 | 9/2008 | Agrawal |
| 2008/0228250 A1 | 9/2008 | Mironer |
| 2008/0234791 A1 | 9/2008 | Arle et al. |
| 2008/0294226 A1 | 11/2008 | Moffitt et al. |
| 2009/0112281 A1 | 4/2009 | Miyazawa et al. |
| 2009/0204173 A1 | 8/2009 | Fang et al. |
| 2009/0270960 A1 | 10/2009 | Zhao et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0125313 A1 | 5/2010 | Lee et al. |
| 2010/0137938 A1 | 6/2010 | Kishawi et al. |
| 2010/0152811 A1 | 6/2010 | Flaherty |
| 2010/0185253 A1 | 7/2010 | Dimarco et al. |
| 2010/0217355 A1 | 8/2010 | Tass et al. |
| 2010/0241191 A1 | 9/2010 | Testerman |
| 2010/0274312 A1 | 10/2010 | Alataris |
| 2010/0312304 A1 | 12/2010 | York et al. |
| 2011/0034977 A1 | 2/2011 | Janik et al. |
| 2011/0054567 A1 | 3/2011 | Lane |
| 2011/0054568 A1 | 3/2011 | Lane |
| 2011/0077660 A1 | 3/2011 | Janik et al. |
| 2011/0130804 A1 | 6/2011 | Lin et al. |
| 2011/0160810 A1 | 6/2011 | Griffith |
| 2011/0184489 A1 | 7/2011 | Nicolelis et al. |
| 2011/0218590 A1 | 9/2011 | Degiorgio |
| 2011/0218594 A1 | 9/2011 | Doron |
| 2011/0224665 A1 | 9/2011 | Crosby et al. |
| 2011/0224753 A1 | 9/2011 | Palermo |
| 2011/0224757 A1 | 9/2011 | Zdeblick et al. |
| 2011/0237921 A1 | 9/2011 | Askin et al. |
| 2012/0035684 A1 | 2/2012 | Thompson et al. |
| 2012/0059432 A1 | 3/2012 | Emborg et al. |
| 2012/0071950 A1 | 3/2012 | Archer |
| 2012/0109251 A1 | 5/2012 | Lebedev |
| 2012/0123293 A1 | 5/2012 | Shah et al. |
| 2012/0136408 A1 | 5/2012 | Grill et al. |
| 2012/0165899 A1 | 6/2012 | Gliner |
| 2012/0172946 A1 | 7/2012 | Altaris et al. |
| 2012/0179222 A1 | 7/2012 | Jaax |
| 2012/0232615 A1 | 9/2012 | Barolat |
| 2012/0277834 A1 | 11/2012 | Mercanzini et al. |
| 2012/0330391 A1 | 12/2012 | Bradley et al. |
| 2013/0030501 A1 | 1/2013 | Feler et al. |
| 2013/0035745 A1 | 2/2013 | Ahmed et al. |
| 2013/0085361 A1 | 4/2013 | Mercanzini et al. |
| 2013/0096640 A1 | 4/2013 | Possover |
| 2013/0123568 A1 | 5/2013 | Hamilton et al. |
| 2013/0253299 A1 | 9/2013 | Weber |
| 2013/0253611 A1 | 9/2013 | Lee |
| 2014/0163640 A1 | 6/2014 | Edgerton et al. |
| 2014/0180361 A1 | 6/2014 | Burdick |
| 2014/0316484 A1 | 10/2014 | Edgerton |
| 2014/0316503 A1 | 10/2014 | Tai |
| 2015/0217120 A1 | 8/2015 | Nandra et al. |
| 2015/0231396 A1 | 8/2015 | Burdick et al. |
| 2016/0030748 A1 | 2/2016 | Edgerton et al. |
| 2016/0121109 A1 | 5/2016 | Edgerton et al. |
| 2016/0175586 A1 | 6/2016 | Edgerton et al. |
| 2016/0220813 A1 | 8/2016 | Edgergton et al. |
| 2016/0310739 A1 | 10/2016 | Burdick et al. |
| 2017/0157389 A1 | 6/2017 | Tai et al. |
| 2018/0185648 A1 | 7/2018 | Nandra et al. |
| 2018/0229037 A1 | 8/2018 | Edgerton et al. |
| 2018/0353755 A1 | 12/2018 | Edgerton et al. |

FOREIGN PATENT DOCUMENTS

| | | |
|---|---|---|
| JP | 2008-067917 A | 3/2008 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| WO | 1997/047357 A1 | 12/1997 |
| WO | 2003/026735 A2 | 4/2003 |
| WO | 2003/092795 A1 | 11/2003 |
| WO | 2004/087116 A2 | 10/2004 |
| WO | 2005/051306 A2 | 6/2005 |
| WO | 2005/087307 A2 | 9/2005 |
| WO | 2007/081764 A2 | 7/2007 |
| WO | 2007/107831 A2 | 9/2007 |
| WO | 2008/070807 A3 | 6/2008 |
| WO | 2008/075294 A1 | 6/2008 |
| WO | 2008/109862 A2 | 9/2008 |
| WO | 2008/121891 A1 | 10/2008 |
| WO | 2009/042217 A1 | 4/2009 |

(56) References Cited

FOREIGN PATENT DOCUMENTS

| WO | 2009/111142 A2 | 9/2009 |
|---|---|---|
| WO | 2010/114998 A1 | 10/2010 |
| WO | 2010/124128 A1 | 10/2010 |
| WO | 2011/005607 A1 | 1/2011 |
| WO | 2012/094346 A2 | 7/2012 |
| WO | 2012/100260 A2 | 7/2012 |
| WO | 2012/129574 A2 | 9/2012 |
| WO | 2013/071307 A1 | 5/2013 |
| WO | 2013/071309 A1 | 5/2013 |
| WO | 2014/144785 A1 | 9/2014 |
| WO | 2015/106286 A1 | 7/2015 |

OTHER PUBLICATIONS

Ganley et al., Epidural spinal cord stimulation improves locomotor performance in low ASIA C, Wheel-chair-Dependent, spinal cord-injured individuals: Insights from metabolic response. Top. Spinal Cord Inj. Rehabil; 11(2); 50-63 (2005).
"Hermann et al., Spinal cord stimulation facilitates functional walking in a chronic, incomplete spinal cord injured. Spinal Cord, vol. 40, pp. 65-68 (2002)."
International Search Report for International Application Serial No. PCT/US2012/020112 filed on Jan. 3, 2012.
International Search Report for International Application Serial No. PCT/US2012/022257 filed on Jan. 23, 2012.
International Search Report for International Application Serial No. PCT/US2012/030624 filed on Mar. 26, 2012.
International Search Report for International Application Serial No. PCT/US2014/029340 filed on Mar. 14, 2014.
Nandra et al., A parylene-based microelectrode arrary implant for spinal cord stimulation in rats. Conf. Proc. IEEE Eng. Met Biol. Soc., pp. 1007-1010 (2011).
Nandra et al., A wireless microelectode implant for spinal cord stimulation and recording in rats. Presentation Abstract, 2013.
Transcutaneous Lumbar Spinal Cord Stimulation, http://www.restrorativeneurology.org (available online and attached), International Society for Restorative Neurology, 2012.
Rodger et al., High density flexible parylene-based multielectrode arrays for retinal and spinal cord stimulation. Proc. of the 14th International Conference on Solid-State Sensors, Actuators and Microsystems, pp. 1385-1888 (2007).
International Search Report for International Application Serial No. PCT/US2012/064874 filed on Nov. 13, 2012.
International Search Report for International Application Serial No. PCT/US2012/064878 filed on Nov. 13, 2012.
Dimitrijevic et al., Clinical elements for the neuromuscular stimulation and functional electrical stimulation protocols in the practice of neurorehabilitation, Artificial Organs, 26(3): 256-259 (2002).
Dimitrijevic et al., Evidence for a spinal central pattern generator in humans. Annals New York Academy Sciences, 860: 360-376 (1998).
Gerasimenko et al., Control of locomotor activity in humans and animals in the absence of supraspinal influences. Neuroscience and Behavioral Physiology, 32(4): 417-423 (2002).
Hofstoetter et al., Modification of reflex responses to lumbar posterior root stimulation by motor tasks in healthy subjects. Artificial Organs, 32(8):644-648 (2008).
Hofstoetter et al., Model of spinal cord reflex circuits in humans: stimulation frequency-dependence of segmental activities and their interactions. Second Congress International Society of Intraoperative Neurophysiology (ISIN), Dubrovnik, Croatia, pp. 8-10 (2009).
International Search Report and Written Opinion dated May 19, 2015 for International Application Serial No. PCT/US2015/011263 filed on Jan. 13, 2015.
Jilge et al, Initiating extension of the lower limbs in subjects with complete spinal cord injury by epidural lumbar cord stimulation. Exp Brain Res., 154: 308-326 (2004).
Ladenbauer et al., Stimulation of the human lumbar spinal cord with implanted and surface electrodes: a computer simulation study. IEEE Transactions on Neural Systems and Rehabilitation Engineering, 18(6):637-645 (2010).
Minassian et al., Transcutaneous stimulation of the human lumbar spinal cord: Facilitating locomotor output in spinal cord injury. Society for Neuroscience, Conference Proceedings, Neuroscience 2010, San Diego, CA, Abstract Viewer/Itinerary Planner No. 286. 19, Abstract & Poster attached (2010).
Minassian et al., Human lumbar cord circuitries can be activated by extrinsic tonic input to generate locomotor-like activity. Human Movement Science, 26(2):275-295 (2007).
Minassian et al., Posterior root-muscle reflexes elicited by transcutaneous stimulation of the human lumbosacral cord. Muscle & Nerve, 35(3):327-336 (2007) Article first published online in 2006.
Minassian et al., Stepping-like movements in humans with complete spinal cord injury induced by epidural stimulation of the lumbar cord: electromyographic study of compound muscle action potentials. Spinal Cord, 42: 401-416 (2004).
Minassian et al., Peripheral and central afferent input to the lumbar cord. Biocybernetics and Biomedical Engineering, 25(3): 11-29 (2005).
Minassian et al., Human lumbar cord model of the locomotor central pattern generator. Second Congress International Society of Intraoperative Neurophysiology (ISIN), Dubrovnik, Croatia, pp. 11-13 (2009).
Minassian et al., Posterior root-muscle reflex, Second Congress International Society of Intraoperative Neurophysiology (ISIN), Dubrovnik, Croatia, pp. 77-80 (2009).
Murg et al., Epidural electric stimulation of posterior structures of the human lumbar spinal cord: Muscle twitches—a functional method to define the site of stimulation, Spinal Cord, 38: 394-402 (2000).
Rattay et al., Epidural electrical stimulation of posterior structures of the human lumbosacral cord: 2. Quantitative analysis by computer modeling. Spinal Cord, 38: 473-489 (2000).
Supplementary European Search Report and Opinion for European Patent Application Serial No. 12848368.2 filed on Nov. 13, 2012.
Ward, Electrical Stimulation Using Kilohertz-Frequency Alternating Current. Physical therapy, 89:181-190 (2009) (published online Dec. 18, 2008).
Minassian et al., Neurophysiology of the human lumbar locomotor pattern generator. 2010. 15th Annual Conference of the International Functional Electrical Stimulation Society. Annual IFESS Conference Proceedings.
Gerasimenko et al., Noninvasive reactivation of motor descending control after paralysis. Journal of Neurotrauma, 2015 (article has been peer-reviewed and accpeted for publication, 49 pages).
Danner et al., Body position influences which neural structures are recruited by lumbar transcutaneous spinal cord stimulation. PLoS ONE 11(1):e0147479 (2016).
Dimitrijevic et al., Electrophysiological characteristics of H-reflexes elicited by percutaneous stimulation of the cauda equina. Abstract No. 4927, 34th Annual Meeting of the Society for Neuroscience, San Diego, CA (2004).
Hofstoetter et al., Modification of spasticity by transcutaneous spinal cord stimulation in individuals with incomplete spinal cord injury. The Journal of Spinal Cord Medicine, 37:2, 202-211 (2014).
Hofstoetter et al., Effects of transcutaneous spinal cord stimulation on voluntary locomotor activity in an Incomplete spinal cord injured individual. Biomed Tech, 58 (Suppl. 1) 2013.
Krenn et al., Selectivity of transcutaneous stimulation of lumbar posterior roots at different spinal levels in humans. Biomed Tech, 58 (Suppl. 1) (2013).
Minassian et al., Mechanisms of rhythm generation of the human lumbar spinal cord in repose to tonic stimulation without and with step-related sensory feedback. Biomed Tech, 58 (Suppl. 1) (2013).
Minassian et al., Neuromodulation of lower limb motor control in restorative neurology. Clinical Neurology and Neurosurgery, 114:489-497 (2012).
Office Action for European Patent Application No. 12760696.0 dated Nov. 9, 2017.
Office Action for Canadian Patent Application No. 2,823,592 dated Oct. 5, 2017.
Office Action for Australian Patent Application No. 2017203132 dated Oct. 13, 2017.
Rasmussen, Carl Edward. Gaussian Processes in Machine Learning. Machine Learning, L.N.A.I. 3176, p. 63-71 (2003).

(56) References Cited

OTHER PUBLICATIONS

U.S. Appl. No. 15/878,325, filed Jan. 23, 2018.
U.S. Appl. No. 15/821,076, filed Nov. 22, 2017.
Office Action for Japanese Patent Application No. 2017-198155 dated Sep. 11, 2018 (original and translation enclosed).
Office Action for Chinese Patent Application No. 201610987062.5 dated Sep. 30, 2018 (original and translation enclosed).
U.S. Office Action for U.S. Appl. No. 15/821,076 dated Oct. 10, 2018.
U.S. Office Action for U.S. Appl. No. 15/713,456 dated Oct. 24, 2018.
U.S. Appl. No. 161189,655, filed Nov. 13, 2018.
U.S. Appl. No. 161153,472, filed Oct. 5, 2018.
Office Action for Canadian Patent Application No. 2,823,592 dated Aug. 20, 2018.
Office Action for Canadian Patent Application No. 2,824,782 dated Oct. 2, 2018.
Office Action for Canadian Patent Application No. 2,825,550 dated Dec. 20, 2018.
Office Action for European Patent Application No. 12732280.8 dated Aug. 24, 2018.
Office Action for Korean Patent Application No. 10-2013-7027989 dated Dec. 14, 2018 (original and translation included).
U.S. Office Action for U.S. Appl. No. 15/232,623 dated Dec. 26, 2018.
Office Action for Canadian Patent Application No. 2,856,202 dated Jun. 19, 2018.
Office Action for European Patent Application No. 12848368.2 dated May 9, 2018.
Office Action for Canadian Patent Application No. 2,824,782 dated Nov. 29, 2017.
Office Action for Australian Patent Application No. 2017221868 dated Jan. 23, 2018.
Office Action for Canadian Patent Application No. 2,825,550 dated Jan. 24, 2018.
U.S. Office Action for U.S. Appl. No. 15/096,014 dated Sep. 14, 2017.
U.S. Office Action for U.S. Appl. No. 14/925,791 dated Jul. 20, 2017.
U.S. Appl. No. 15/713,456, filed Sep. 22, 2017.
Examiner's Report—CA Application No. 2825550 dated Dec. 13, 2019—6 pages.

* cited by examiner

NEUROSTIMULATOR

PRIORITY

This application is a continuation of U.S. patent application Ser. No. 15/199,580, filed Jun. 30, 2016, now U.S. Pat. No. 9,931,508, which is a continuation of U.S. patent application Ser. No. 14/007,262, filed Feb. 17, 2014, now U.S. Pat. No. 9,409,023, which is a national phase filing of PCT Application No. PCT/US12/30624, filed Mar. 26, 2012, which claims the benefit of U.S. Provisional Application No. 61/467,107, filed Mar. 24, 2011, each of which is incorporated herein by reference in its entirety.

STATEMENT REGARDING FEDERALLY SPONSORED RESEARCH OR DEVELOPMENT

This invention was made with Government support under Grant No. EB007615, awarded by the National Institutes of Health. The Government has certain rights in this invention.

BACKGROUND OF THE INVENTION

Field of the Invention

The present invention is directed generally to the field of medical electro-medical therapy devices, and more particularly to implantable stimulators and stimulator systems used in neurological rehabilitation for the treatment of traumatic and non-traumatic injury or illness.

Description of the Related Art

Prior art implantable neurostimulator devices have been used to deliver therapy to patients to treat a variety of symptoms or conditions such as chronic pain, epilepsy, and tremor associated with and without Parkinson's disease. The implantable stimulators deliver stimulation therapy to targeted areas of the nervous system. The applied therapy is usually in the form of electrical pulse at a set frequency. The current is produced by a generator. The generator and an associated control module may be constructed from a variety of mechanical and electrical components. The generator is typically housed in a casing made of biocompatible material such as titanium, allowing for surgical placement subcutaneously within the abdomen or chest wall of a patient by someone with ordinary skill in the art of orthopedic spine and neurosurgery.

The stimulator is attached via one or more leads to one or more electrodes that are placed in close proximity to one or more nerves, one or more parts of a nerve, one or more nerve roots, the spinal cord, the brain stem, or within the brain itself. The leads and electrode arrays may vary in length, and are also made of a biocompatible material.

Historically, implantable stimulators and their attached electrodes positioned outside of the brain around the spinal cord, nerve roots, spinal nerves, and peripheral nerves have been used to manage and treat chronic pain; none to date have been commercially used or approved to restore function. Further, none have been aimed at permanent remodeling of the nervous system. Attempts to restore function in neurologically impaired subjects have been limited to adjunctive modalities, such as physical and occupational therapy with emphasis on adaptation to disability. Little progress has been achieved in actually restoring normal functional capacity to damaged nerve tissue with the use of an implantable neurostimulator.

Impressive levels of standing and stepping recovery have been demonstrated in certain incomplete spinal cord injury ("SCI") subjects with task specific physical rehabilitation training. A recent clinical trial demonstrated that 92% of the subjects regained stepping ability to almost a functional speed of walking three months after a severe yet incomplete injury. Dobkin et al. (2006) *Neurology*, 66(4): 484-93. Furthermore, improved coordination of motor pool activation can be achieved with training in patients with incomplete SCI. Field-Fote et al. (2002) *Phys. Ther.*, 82 (7): 707-715.

On the other hand, there is no generally accepted evidence that an individual with a clinically complete SCI can be trained to the point where they can stand or locomote even with the aid of a "walker." Wernig (2005) *Arch Phys Med Rehabil.*, 86(12): 2385-238. Further, no one has shown the ability to regain voluntary movements, and/or to recover autonomic, sexual, vasomotor, and/or improved cognitive function after a motor complete SCI.

Therefore, a need exists for a neurostimulator device configured to deliver stimulation through an electrode array that will help a patient regain voluntary movements, and/or recover autonomic, sexual, vasomotor, and/or improved cognitive function after a motor incomplete SCI or motor complete SCI. The present application provides these and other advantages as will be apparent from the following detailed description and accompanying figures.

SUMMARY OF THE INVENTION

Embodiments include a neurostimulator device for use with a subject (e.g., a human patient or an animal). The neurostimulator device may be for use with a plurality of groups of electrodes. In particular implementations, the plurality of groups of electrodes may include more than four groups of electrodes. The neurostimulator device may include a stimulation assembly connectable to the plurality of groups of electrodes. The stimulation assembly is configured to deliver different stimulation to each of the plurality of groups of electrodes when the stimulation assembly is connected thereto. The neurostimulator device may also include at least one processor connected to the stimulation assembly. The at least one processor is configured to direct the stimulation assembly to deliver the different stimulation to each of the plurality of groups of electrodes. The neurostimulator device may be configured for implantation in a subject (e.g., a human being or an animal). The stimulation delivered to at least one of the plurality of groups of electrodes may include one or more waveform shapes other than a square or rectangular wave shape.

In other embodiments, the neurostimulator device is for use with a plurality of electrodes, and one or more sensors. In such embodiments, the neurostimulator device may include a stimulation assembly connectable to the plurality of electrodes. The stimulation assembly is configured to deliver stimulation to selected ones of the plurality of electrodes when the stimulation assembly is connected to the plurality of electrodes. The neurostimulator device may also include a sensor interface connectable to the one or more sensors. The sensor interface is configured to receive signals from the one or more sensors when the sensor interface is connected to the one or more sensors. The neurostimulator device may further include at least one processor connected to both the stimulation assembly and the sensor interface. The at least one processor is configured to direct the stimulation assembly to deliver at least one complex stimulation pattern to the selected ones of the plurality of electrodes, and to receive the signals from the sensor interface. The at least one processor is further configured to modify the at least one complex stimulation pattern delivered by the stimulation assembly based on the signals received from the sensor interface. In some embodiments, the stimulation assembly, sensor interface, and at least one processor are housed inside a housing configured for implantation in the body of the subject.

The at least one complex stimulation pattern may include a first stimulation pattern followed by a second stimulation pattern. In such embodiments, the second stimulation pattern may be delivered to a second portion of the selected ones of the plurality of electrodes less than about one microsecond after the first stimulation pattern is delivered to a first portion of the selected ones of the plurality of electrodes. Optionally, the first stimulation pattern may be delivered to a first portion of the selected ones of the plurality of electrodes, and the second stimulation pattern is delivered to a second portion of the selected ones of the plurality of electrodes, wherein the first portion is different from the second portion. The selected ones of the plurality of electrodes may include more than four groups of electrodes, and the at least one complex stimulation pattern may include different electrical stimulation for each of the groups of electrodes.

The at least one processor may be configured to perform a machine learning method (based on the signals received from the sensor interface) to determine a set of stimulation parameters. In such embodiments, the at least one processor may modify the at least one complex stimulation pattern based at least in part on the set of stimulation parameters. Optionally, the at least one processor may be configured to receive and record electrical signals from the plurality of electrodes. The at least one processor may modify the at least one complex stimulation pattern based at least in part on the electrical signals received from the plurality of electrodes.

The at least one processor may include at least one of a microprocessor, a microcontroller, a field programmable gate array, and a digital signal processing engine.

The neurostimulator device may be for use with a computing device. In such embodiments, the at least one processor may be configured to transmit the recorded electrical signals to the computing device and to receive information therefrom. The at least one processor may be configured to modify the at least one complex stimulation pattern based at least in part on the information received from the computing device. Optionally, the at least one processor may be configured to record the signals received from the sensor interface, transmit the recorded electrical signals to the computing device, and receive information from the computing device. The at least one processor may be configured to modify the at least one complex stimulation pattern based at least in part on the information received from the computing device.

The plurality of sensors may include at least one of an Electromyography sensor, a joint angle sensor, an accelerometer, a gyroscope sensor, a flow sensor, a pressure sensor, and a load sensor.

Embodiments of the neurostimulator devices may be for use with a subject having a neurologically derived paralysis in a portion of the patient's body. The subject has a spinal cord with at least one selected spinal circuit that has a first stimulation threshold representing a minimum amount of stimulation required to activate the at least one selected spinal circuit, and a second stimulation threshold representing an amount of stimulation above which the at least one selected spinal circuit is fully activated. When the at least one complex stimulation pattern is applied to a portion of a spinal cord of the patient, the at least one complex stimulation pattern is below the second stimulation threshold such that the at least one selected spinal circuit is at least partially activatable by the addition of at least one of (a) neurological signals originating from the portion of the patient's body having the paralysis, and (b) supraspinal signals. The neurological signals originating from the portion of the patient's body having the paralysis may be induced neurological signals induced by physical training. The induced neurological signals may include at least one of postural proprioceptive signals, locomotor proprioceptive signals, and the supraspinal signals.

In some embodiments, when at least partially activated, the at least one selected spinal circuit produces improved neurological function including at least one of voluntary movement of muscles involved in at least one of standing, stepping, reaching, grasping, voluntarily changing positions of one or both legs, voluntarily changing positions of one or both arms, voiding the subject's bladder, voiding the subject's bowel, postural activity, and locomotor activity. In some embodiments, when at least partially activated, the at least one selected spinal circuit produces improved neurological function including at least one of improved autonomic control of at least one of voiding the subject's bladder, voiding the subject's bowel, cardiovascular function, respiratory function, digestive function, body temperature, and metabolic processes. In some embodiments, when at least partially activated the at least one selected spinal circuit produces improved neurological function including at least one of an autonomic function, sexual function, motor function, vasomotor function, and cognitive function.

Optionally, the neurostimulator device may include at least one rechargeable battery configured to power the at least one processor, and a wireless recharging assembly configured to receive power wirelessly and transmit at least a portion of the power received to the at least one rechargeable battery.

The neurostimulator device may be for use with a plurality of muscle electrodes. In such embodiments, the neurostimulator device may include a muscle stimulation assembly connected to the at least one processor, and configured to deliver electrical stimulation to the plurality of muscle electrodes. In such embodiments, the at least one processor may be configured to instruct the muscle stimulation assembly to deliver the electrical stimulation to the plurality of muscle electrodes. In alternate embodiments, the neurostimulator device may be for use with a muscle stimulation device configured to deliver electrical stimulation to the plurality of muscle electrodes. In such embodiments, the neurostimulator device may include an interface connected to the at least one processor, and configured to direct the muscle stimulation device to deliver electrical stimulation to the plurality of muscle electrodes.

Optionally, the neurostimulator device may be for use with at least one recording electrode. In such embodiments, the at least one processor is connected to the at least one recording electrode, and configured to receive and record electrical signals received from the at least one recording electrode.

The neurostimulator devices described above may be incorporated in one or more systems. An example of such a system may be for use with a subject having body tissue, and one or more sensors positioned to collect physiological data related to the subject. The system may include a plurality of electrodes, the neurostimulator device, and a computing device. The plurality of electrodes may be arranged in an electrode array implantable adjacent the body tissue of the subject. The electrode array may be implantable adjacent at least one of a portion of the spinal cord, one or more spinal nerves, one or more nerve roots, one or more peripheral nerves, the brain stem, the brain, and an end organ. The plurality of electrodes may include at least 16 electrodes. The electrode array may be implantable along a portion of the dura of the spinal cord of the subject. The electrode array may be a high-density electrode array in which adjacent ones of the plurality of electrodes are positioned within 300 micrometers of each other.

The neurostimulator device may be connected to the plurality of electrodes and configured to deliver complex stimulation patterns thereto. The computing device may be configured to transmit stimulation parameters to the neurostimulator device. The neurostimulator device may be configured to generate the complex stimulation patterns based at least in part on the stimulation parameters received from the computing device. The computing device may be further configured to determine the stimulation parameters based on at least in part on the physiological data collected by the one or more sensors. The stimulation parameters may identify a waveform shape, amplitude, frequency, and relative phasing of one or more electrical pulses delivered to one or more pairs of the plurality of electrodes. Each of the complex stimulation patterns may include a plurality of different electrical signals each delivered to a different pair of the plurality of electrodes.

The computing device may be configured to perform a machine learning method operable to determine the stimulation parameters. The machine learning method may implement a Gaussian Process Optimization.

The neurostimulator device may be configured to generate the complex stimulation patterns based at least in part on one or more stimulation parameters determined by the neurostimulator device. In such embodiments, the neurostimulator device may be configured to perform a machine learning method operable to determine the one or more stimulation parameters. The machine learning method may implement a Gaussian Process Optimization.

The one or more sensors may include at least one of a surface EMG electrode, a foot force plate sensor, an in-shoe sensor, an accelerator, and a gyroscope sensor attached to or positioned adjacent the body of the subject. The one or more sensors may include a motion capture system.

The neurostimulator device may be connected to the one or more sensors, and configured to transmit the physiological data collected by the one or more sensors to the computing device. The computing device may be connected to the one or more sensors, and configured to receive the physiological data from the one or more sensors.

The system may be for use with the subject having a body, a spinal cord, and a neurologically derived paralysis in a portion of the subject's body. The spinal cord has at least one selected spinal circuit that has a first stimulation threshold representing a minimum amount of stimulation required to activate the at least one selected spinal circuit, and a second stimulation threshold representing an amount of stimulation above which the at least one selected spinal circuit is fully activated. The system may include a training device configured to physically train the subject and thereby induce induced neurological signals in the portion of the patient's body having the paralysis. The induced neurological signals are below the first stimulation threshold and insufficient to activate the at least one selected spinal circuit. The complex stimulation patterns are below the second stimulation threshold such that the at least one selected spinal circuit is at least partially activatable by the addition of at least one of (a) a portion of the induced neurological signals, and (b) supraspinal signals.

Optionally, the system may include at least one recording electrode connected to the neurostimulator device. In such embodiments, the neurostimulator device is configured to receive and record electrical signals received from the at least one recording electrode. The at least one recording electrode may be positioned on the electrode array. The electrode array may be considered a first electrode array, and the system may include a second electrode array. The at least one recording electrode may be positioned on at least one of the first electrode array and the second electrode array.

Optionally, the system may include a plurality of muscle electrodes. In such embodiment, the neurostimulator device may include a muscle stimulation assembly configured to deliver electrical stimulation to the plurality of muscle electrodes. Alternatively, the system may be for use with a plurality of muscle electrodes and a muscle stimulation device configured to deliver electrical stimulation to the plurality of muscle electrodes. In such embodiments, the neurostimulator device may include an interface configured to direct the muscle stimulation device to deliver electrical stimulation to the plurality of muscle electrodes.

Another example of a system including at least one of the neurostimulator devices described above is for use with a network and a subject having body tissue, and one or more sensors positioned to collect physiological data related to the subject. The system includes a plurality of electrodes, the neurostimulator device, a first computing device, and a remote second computing device. The plurality of electrodes may be arranged in an electrode array implantable adjacent the body tissue of the subject. The neurostimulator device is connected to the plurality of electrodes and configured to deliver complex stimulation patterns thereto. The first computing device is connected to the network and configured to transmit stimulation parameters to the neurostimulator device. The neurostimulator device is configured to generate the complex stimulation patterns based at least in part on the stimulation parameters received from the first computing device. The remote second computing device is connected to the network. The first computing device is being configured to transmit the physiological data collected by the one or more sensors to the second computing device. The second computing device is configured to determine the stimulation parameters based at least in part on the physiological data collected by the one or more sensors, and transmit the stimulation parameters to the first computing device. In some embodiments, the first computing device is configured to receive instructions from the second computing device and transmit them to the neurostimulator device. The first computing device may be configured to receive data from the neurostimulator device and communicate the data to the second computing device over the network.

BRIEF DESCRIPTION OF THE SEVERAL VIEWS OF THE DRAWING(S)

FIG. 4A illustrates a non-rectangular waveform and FIG. 4B illustrates a waveform including small prepulses.

Figure 13:
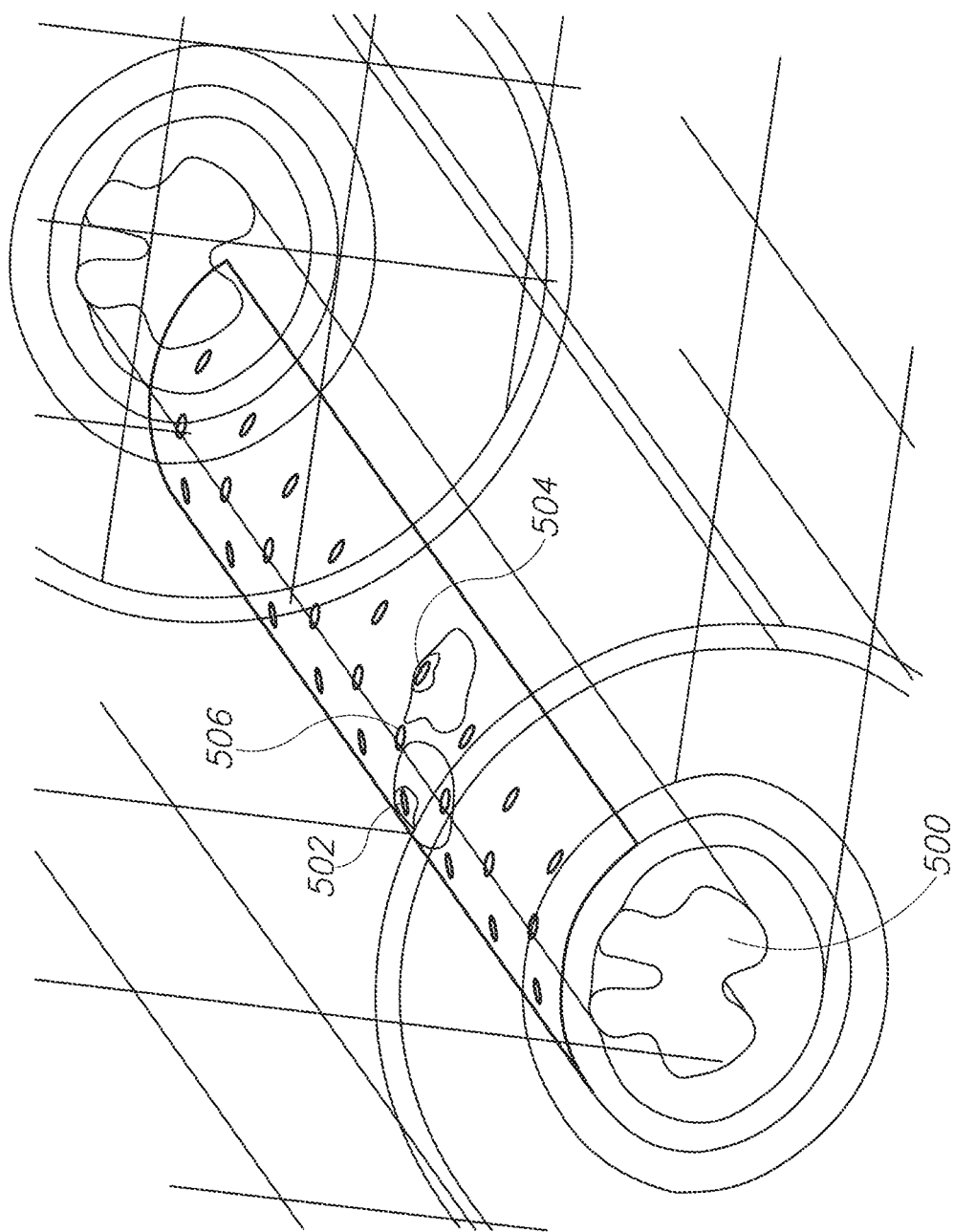
FIG. 13 is an illustration of a multi-compartment physical model of electrical properties of a mammalian spinal cord, along with a 27 electrode implementation of the electrode array placed in an epidural position.
Figure 14:
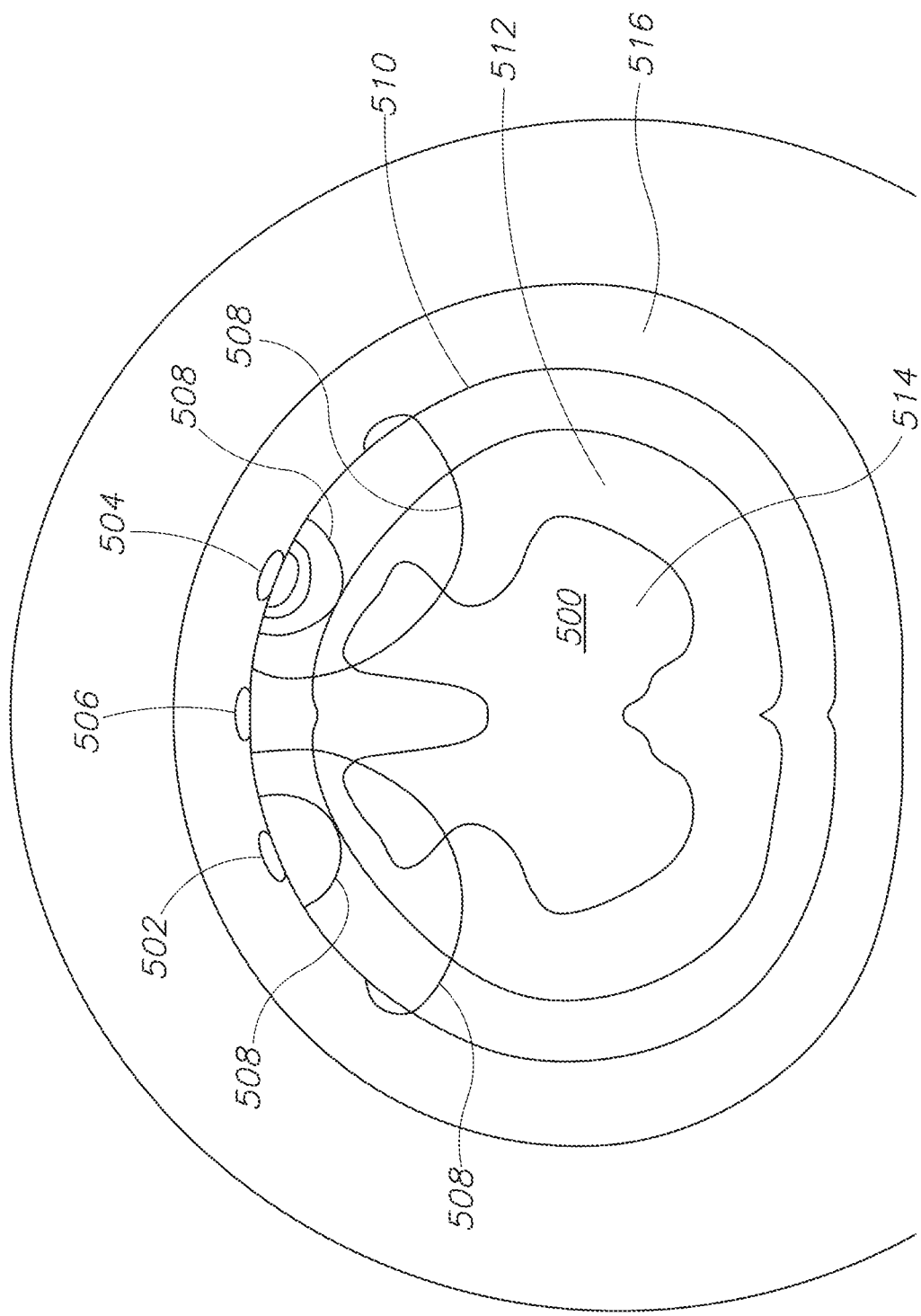
FIG. 14 is a lateral cross-section through the model of the mammalian spinal cord depicted in FIG. 13 cutting through bipolarly activated electrodes showing isopotential contours of the stimulating electric field for the 2-electrode stimulation example.
Figure 15:
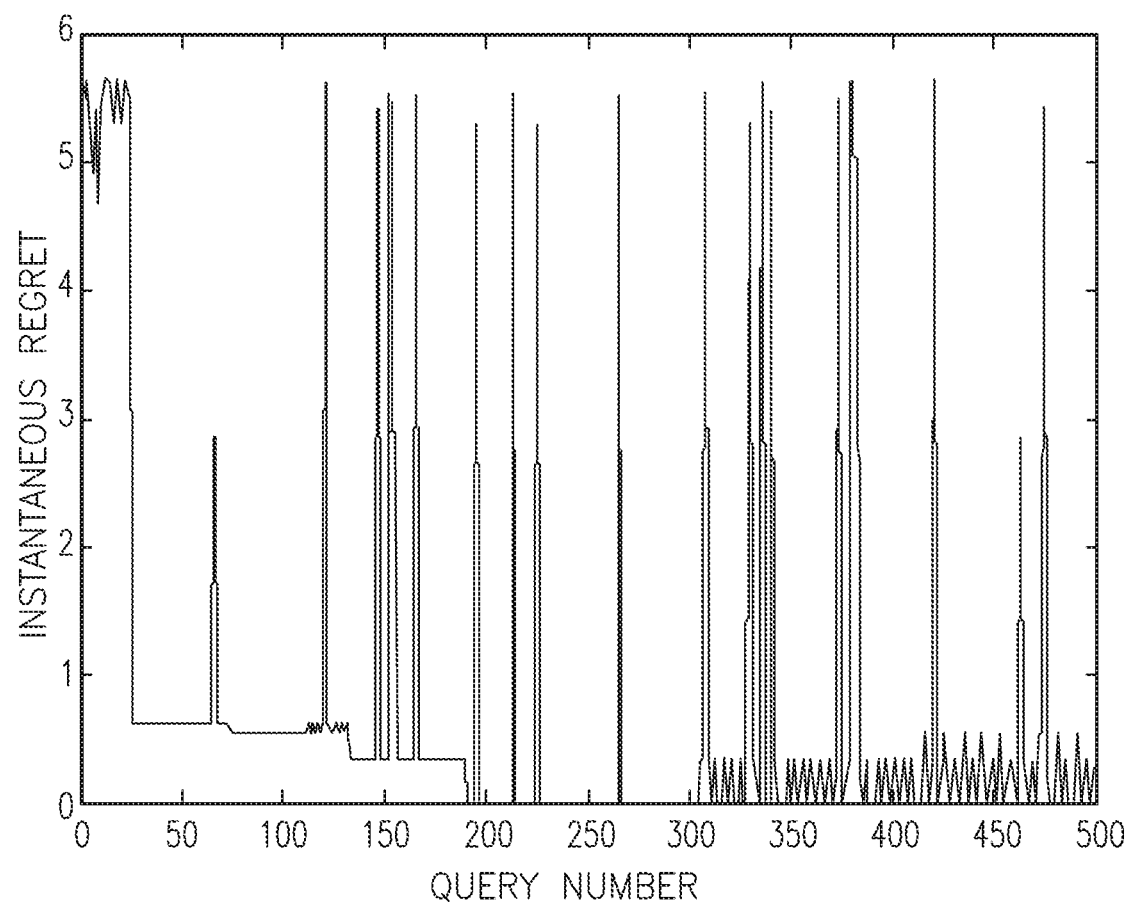

FIG. 15 shows instantaneous regret (a measure of machine learning error) vs. learning iteration (labeled as "query number") for Gaussian Process Optimization of array stimulation parameters in the simulated spinal cord of FIGS. 13 and 14. The "bursts" of poor performance corresponds to excursions of the learning algorithm to regions of parameter space that are previously unexplored, but which are found to have poor performance.

Figure 16:
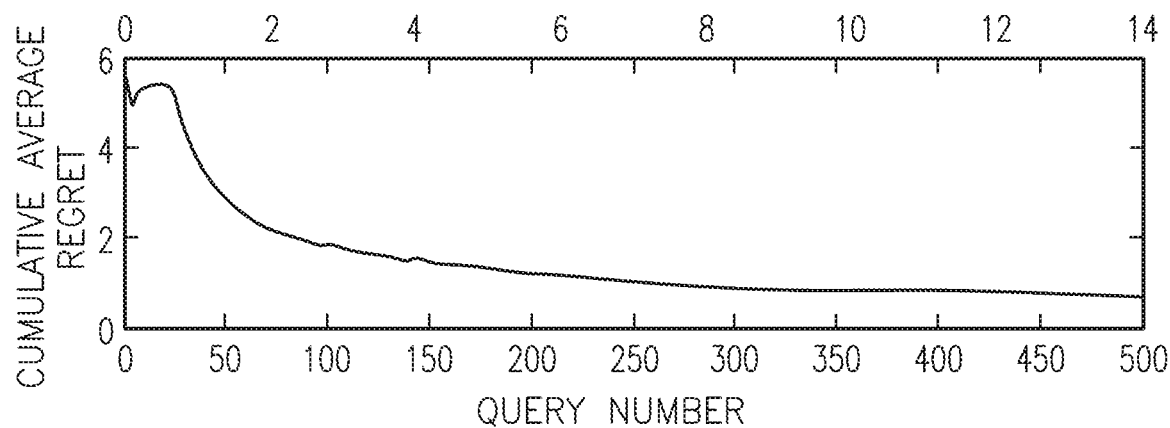

FIG. 16 shows the average cumulative regret vs. learning iteration. The average cumulative regret is a smoothed version of the regret performance function which better shows the algorithm's overall progress in selecting optimal stimulation parameters.

Figure 2:
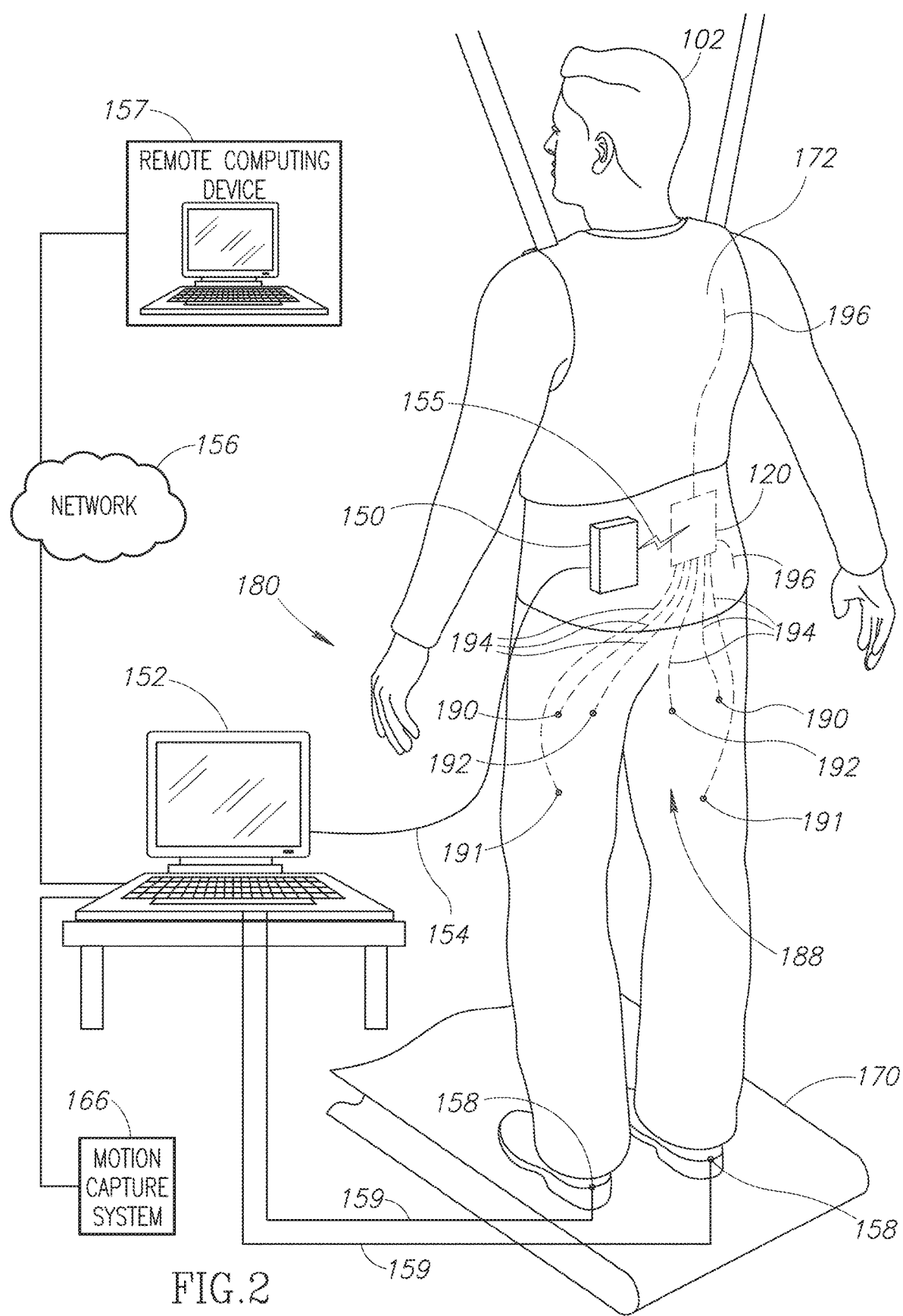
FIG. 2 is an illustration of a system incorporating the implantable assembly of FIG. 1.
Figure 17:
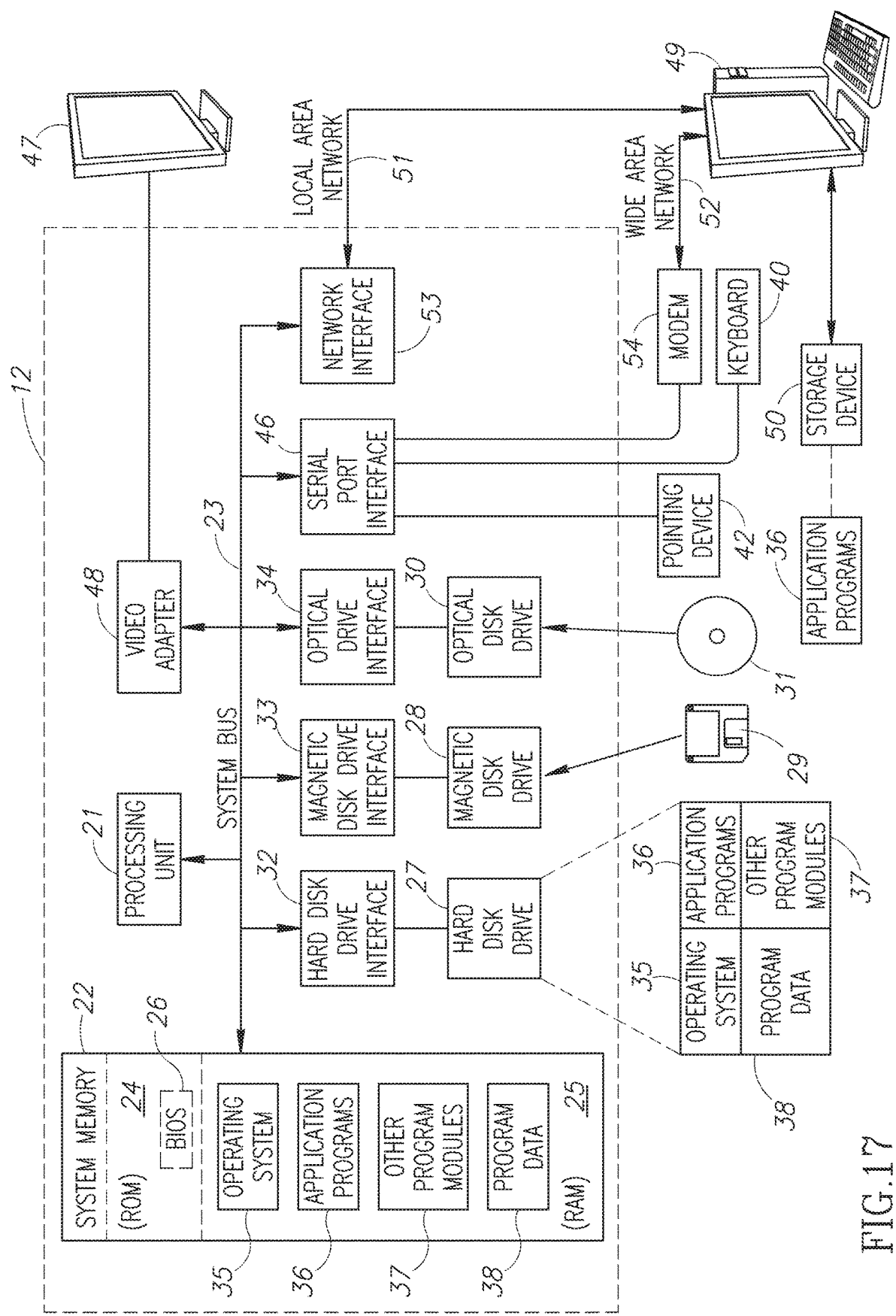

FIG. 17 is a diagram of a hardware environment and an operating environment in which the computing device of the system of FIG. 2 may be implemented.

DETAILED DESCRIPTION OF THE INVENTION

All publications (including published patent applications and issued patents) cited herein are incorporated by reference to the same extent as if each individual publication or patent application was specifically and individually indicated as being incorporated by reference. The following description includes information that may be useful in understanding the technology. The description is not an admission that any of the information provided herein is prior art, or that any publication specifically or implicitly referenced is prior art.

OVERVIEW

Research has shown that the most effective method for improving function after a spinal cord injury ("SCI") is to combine different strategies, as neurological deficits (such as those caused by SCI) are complex, and there is wide variability in the deficit profiles among patients. These strategies include physical therapy, along with electrical stimulation (e.g., high-density epidural stimulation), and optionally one or more serotonergic agents, dopaminergic agents, noradregeneric agents, GABAergic agents, and and/ or glycinergic agents. It is believed such combination strategies facilitate modulation of electrophysiological properties of spinal circuits in a subject so they are activated by proprioceptive input and indirectly use voluntary control of spinal cord circuits not normally available to connect the brain to the spinal cord. In other words, these strategies exploit the spinal circuitry and its ability to interpret proprioceptive information, and respond to that proprioceptive information in a functional way.

Figure 1:
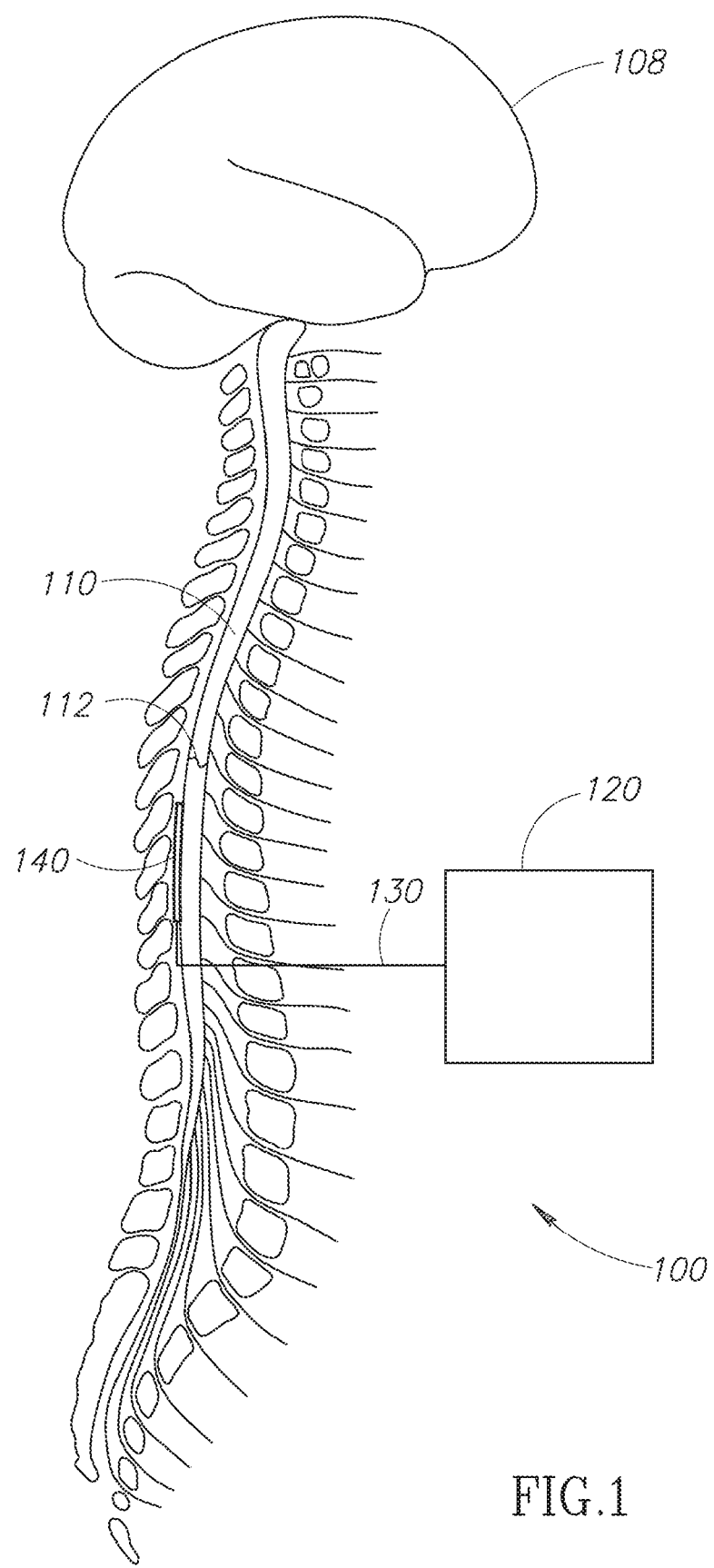
FIG. 1 is an illustration of an implantable assembly.

FIG. 1 illustrates an implantable electrode array assembly 100. While the embodiment of the assembly 100 illustrated is configured for implantation in the human subject 102 (see FIG. 2), embodiments may be constructed for use in other subjects, such as other mammals, including rats, and such embodiments are within the scope of the present teachings. The subject 102 has a brain 108, a spinal cord 110 with at least one selected spinal circuit (not shown), and a neurologically derived paralysis in a portion of the subject's body. In the example discussed herein, the spinal cord 110 of the subject 102 has a lesion 112.

By way of non-limiting examples, when activated, the selected spinal circuit may (a) enable voluntary movement of muscles involved in at least one of standing, stepping, reaching, grasping, voluntarily changing positions of one or both legs and/or one or both arms, voiding the subject's bladder, voiding the subject's bowel, postural activity, and locomotor activity; (b) enable or improve autonomic control of at least one of cardiovascular function, body temperature, and metabolic processes; and/or (c) help facilitate recovery of at least one of an autonomic function, sexual function, vasomotor function, and cognitive function. The effects of activation of the selected spinal circuit will be referred to as "improved neurological function."

Without being limited by theory, it is believed that the selected spinal circuit has a first stimulation threshold representing a minimum amount of stimulation required to activate the selected spinal circuit, and a second stimulation threshold representing an amount of stimulation above which the selected spinal circuit is fully activated and adding the induced neurological signals has no additional effect on the at least one selected spinal circuit.

The paralysis may be a motor complete paralysis or a motor incomplete paralysis. The paralysis may have been caused by a SCI classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative brain injury. The neurodegenerative brain injury may be associated with at least one of Parkinson's disease, Huntington's disease, Dystonia, Alzheimer's, ischemia, stroke, amyotrophic lateral sclerosis (ALS), primary lateral sclerosis (PLS), and cerebral palsy.

Neurological signals may be induced in the paralyzed portion of the subject's body (e.g., by physical training). However, adding the induced neurological signals may have little or no additional effect on the selected spinal circuit, if the induced neurological signals are below the first stimulation threshold and insufficient to activate the at least one selected spinal circuit.

The assembly 100 is configured to apply electrical stimulation to neurological tissue (e.g., a portion of the spinal cord 110, one or more spinal nerves, one or more nerve roots, one or more peripheral nerves, the brain stem, and/or the brain 108, and the like). Further, the electrical stimulation may be applied to other types of tissue, including the tissue of one or more end organs (e.g., bladder, kidneys, heart, liver, and the like). For ease of illustration, the electrical stimulation will be described as being delivered to body tissue. While the stimulation may be delivered to body tissue that is not neurological tissue, the target of the stimulation is generally a component of the nervous system that is modified by the addition of the stimulation to the body tissue.

The electrical stimulation delivered is configured to be below the second stimulation threshold such that the selected spinal circuit is at least partially activatable by the addition of (a) induced neurological signals (e.g., neurological signals induced through physical training), and/or (b) supraspinal signals. By way of a non-limiting example, the assembly 100 may be used to perform methods described in U.S. patent application Ser. No. 13/342,903, filed Jan. 3, 2012, and titled High Density Epidural Stimulation for Facilitation of Locomotion, Posture, Voluntary Movement, and Recovery of Autonomic, Sexual, Vasomotor and Cognitive Function after Neurological Injury, which is incorporated herein by reference in its entirety. However, the selected spinal circuit may be at least partially activatable by the addition neurological signals other than those induced by physical training.

The assembly 100 includes one or more electrode arrays 140, one or more leads 130, and a neurostimulator device 120. For ease of illustration, the one or more electrode arrays 140 will be described as including a single electrode array. However, through application of ordinary skill to the present teachings, embodiments may be constructed that include two or more electrode arrays. Therefore, such embodiments are within the scope of the present teachings. The neurostimulator device 120 generates electrical stimulation that is delivered to the electrode array 140 by the one or more leads 130. Depending upon the implementation details, the neurostimulator device 120 may be characterized as being a neuromodulator device.

The electrode array 140 may be implemented using commercially available high-density electrode arrays designed and approved for implementation in human patients. By way of a non-limiting example, a Medtronic Specify 5-6-5 multi-electrode array (incorporating 16 electrodes) may be used. Examples of suitable electrode arrays include paddle-shaped electrodes (e.g., having a 5-6-5 electrode configuration) constructed from platinum wire and surface electrodes embedded in silicone. Further, the electrode array 140 may be implemented using multiple electrode arrays (e.g., multiple 16-electrode arrays connected to the neurostimulator device 120 in a serial or parallel arrangement).

Figure 3A:
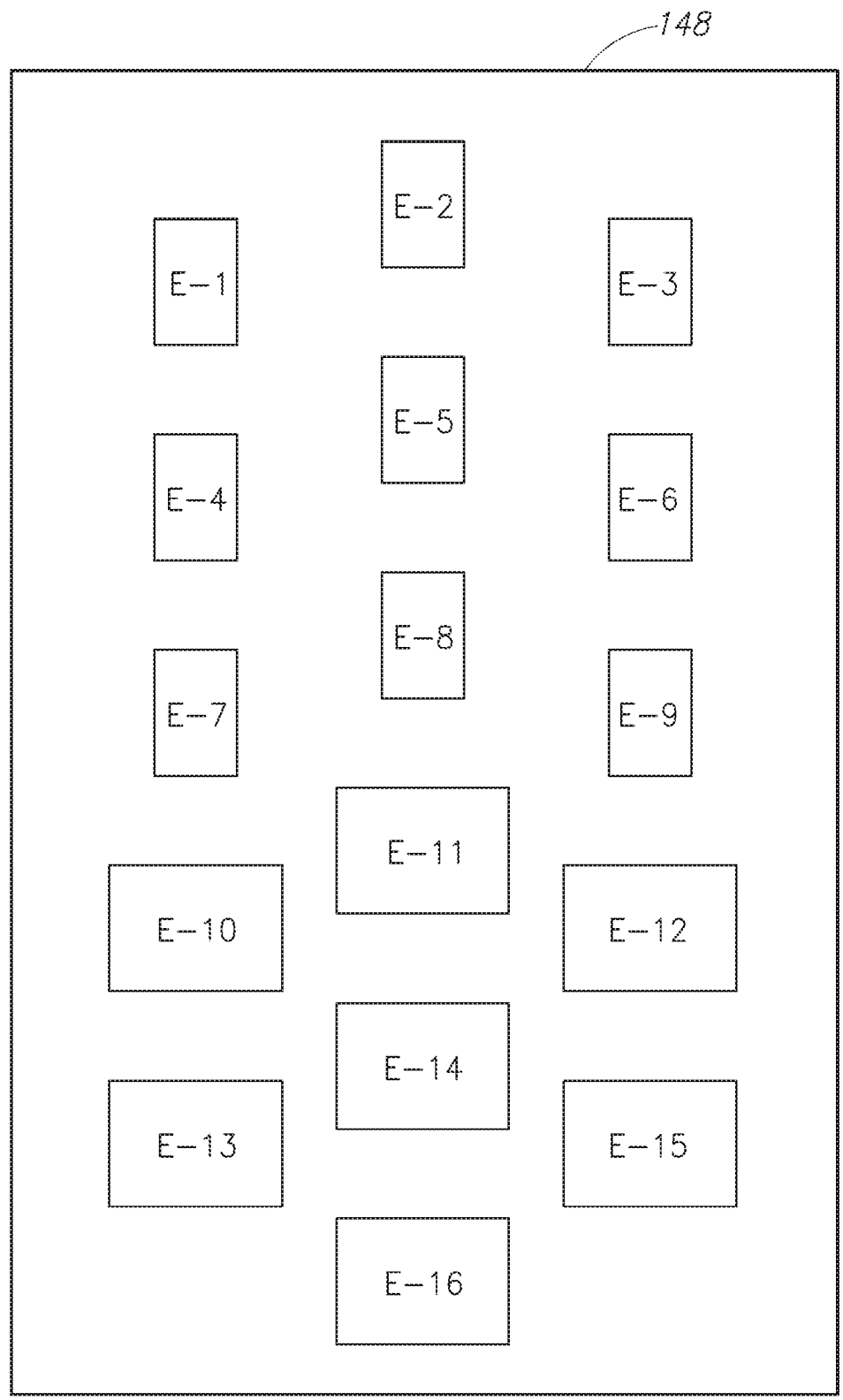
FIG. 3A is an illustration of a first embodiment of an exemplary electrode array for use with the neurostimulator device of the implantable assembly of FIG. 1.

FIG. 3A illustrates a prior art electrode array 148 having 16 electrodes "E-1" to "E-16." The electrode array 140 may be implemented using the electrode array 148. Prior art stimulators allow a user (e.g., a clinician) to divide the electrodes "E-1" to "E-16" into up to four groups. Each group may include any number of electrodes. Stimulation having different frequency and pulse width may be delivered to the groups. In contrast, the neurostimulator device 120 may divide the electrodes "E-1" to "E-16" into any number of groups. For example, each electrode may be assigned to its own group. By way of another example, one or more electrodes may belong to multiple groups. Table A below provides a few examples of groups that may be identified and stimulated independently. Which electrodes function as the anode and which function as a cathode are also specified for illustrative purposes.

TABLE A

| Group Number | Anode electrodes | Cathode electrodes |
| --- | --- | --- |
| 1 | 1 | 3 |
| 2 | 1 and 2 | 3, 4, 5, and 6 |
| 3 | 1, 2, and 3 | 13, 16, and 15 |
| 4 | 1, 2, and 3 | 6, 7, 8, and 9 |

Further, prior art stimulators are configured to deliver only rectangular waves to the electrodes "E-1" to "E-16." In contrast and as will be described in detail below, the neurostimulator device 120 is configured to deliver stimulation having waveform shapes beyond merely rectangular waves.

In particular embodiments, the neurostimulator device 120 is configured to deliver stimulation to a single selected one of the electrodes 142 and/or use a single selected one of the electrodes 142 as a reference electrode. Prior art stimulators are not capable of this level of addressability.

In some embodiments, the electrode array 140 may be constructed using microfabrication technology to place numerous electrodes in an array configuration on a flexible substrate. One suitable epidural array fabrication method was first developed for retinal stimulating arrays (see, e.g., Maynard, *Annu. Rev. Biomed. Eng.*, 3: 145-168 (2001); Weiland and Humayun, *IEEE Eng. Med. Biol. Mag.*, 24(5): 14-21 (2005)), and U.S. Patent Publications 2006/0003090 and 2007/0142878 which are incorporated herein by reference for all purposes (e.g., the devices and fabrication methods disclosed therein). In various embodiments the stimulating arrays comprise one or more biocompatible metals (e.g., gold, platinum, chromium, titanium, iridium, tungsten, and/or oxides and/or alloys thereof) disposed on a flexible material (e.g., parylene A, parylene C, parylene AM, parylene F, parylene N, parylene D, or other flexible substrate materials). Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, *Medical Device and Diagnostic Industry*, 22(8): 42-49 (2000)), and has flexibility characteristics (Young's modulus ~4 GPa (Rodger and Tai, *IEEE Eng. Med. Biology*, 24(5): 52-57 (2005))), lying in between those of PDMS (often considered too flexible) and most polyimides (often considered too stiff). Finally, the tear resistance and elongation at break of parylene are both large, minimizing damage to electrode arrays under surgical manipulation (Rodger et al., *Sensors and Actuators B-Chemical*, 117(1): 107-114 (2006)).

Figure 3B:
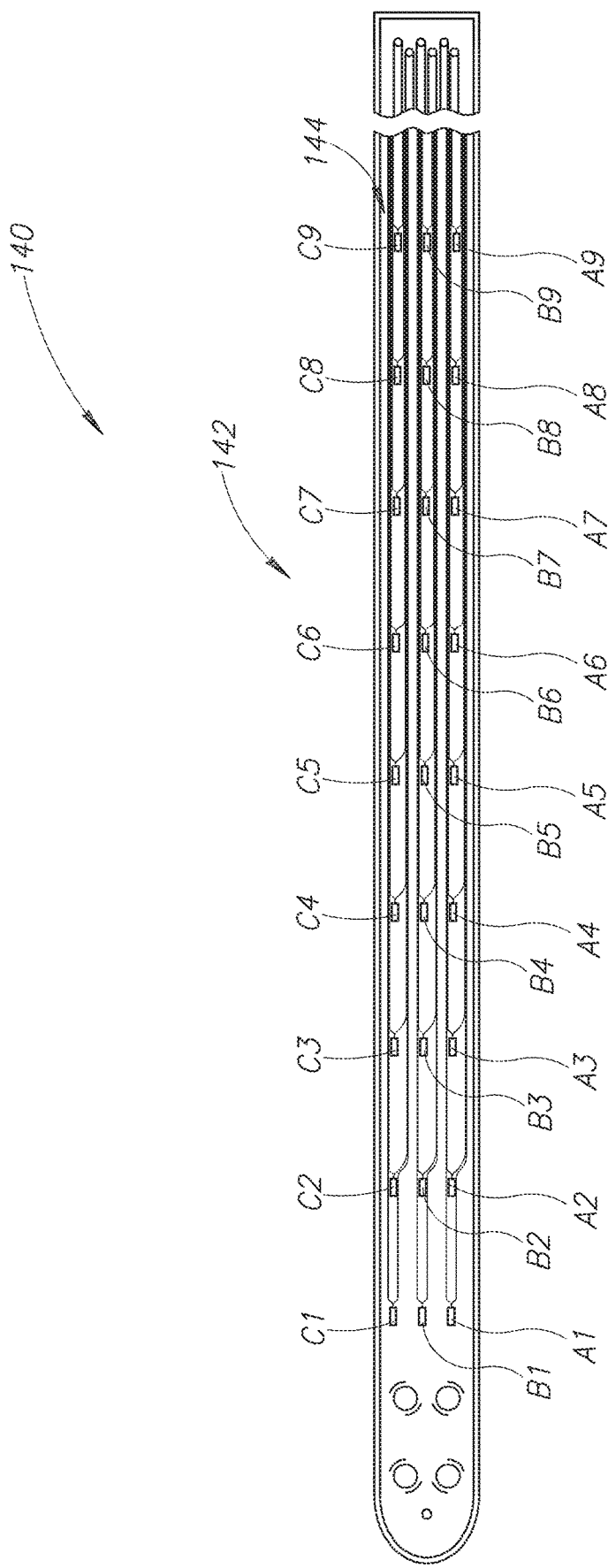
FIG. 3B is an illustration of a second embodiment of an exemplary electrode array for use with the neurostimulator device of the implantable assembly of FIG. 1.

In the embodiment illustrated in FIG. 3, the electrode array 140 may be characterized as being a microelectromechanical systems ("MEMS") device. While the implementation of the electrode array 140 illustrated in FIG. 3 may be suited for use in animals, the basic geometry and fabrication technique can be scaled for use in humans. The electrode array 140 is configured for implantation along the spinal cord 110 (see FIG. 1) and to provide electrical stimulation thereto. For example, the electrode array 140 may provide epidural stimulation to the spinal cord 110. The electrode array 140 allows for a high degree of freedom and specificity in selecting the site of stimulation compared to prior art wire-based implants, and triggers varied biological responses that can lead to an increased understanding of the spinal cord 110 and improved neurological function in the subject 102. A non-limiting example of an electrode array that may be used to construct the electrode array 140 is described in co-pending U.S. patent application Ser. No. 13/356,499, filed on Jan. 23, 2012, and titled Parylene-Based Microelectrode Array Implant for Spinal Cord Stimulation, which is incorporated herein by reference in its entirety.

Turning to FIG. 3, the electrode array 140 includes a plurality of electrodes 142 (e.g., electrodes A1-A9, B1-B9, and C1-C9), and a plurality of electrically conductive traces 144. The electrodes 142 may vary in size, and be constructed using a biocompatible substantially electrically conductive material (such as platinum, Ag/AgCl, and the like), embedded in or positioned on a biocompatible substantially electrically non-conductive (or insulating) material (e.g., flexible parylene). One or more of the traces 144 is connected to each of the electrodes 142. Connecting more than one of the traces 144 to each of the electrodes 142 may help ensure signals reach and are received from each of the electrodes 142. In other words, redundancy may be used to improve reliability. Each of the electrodes 142 has one or more electrically conductive contacts (not shown) positionable alongside body tissue. The body tissue may include neurological tissue (e.g., the spinal cord 110, one or more spinal nerves, one or more nerve roots, one or more peripheral nerves, the brain stem, and/or the brain 108, and the like), other types of spinal tissue (e.g., the dura of the spinal cord 110), and the tissue of end organs. Further, the electrode array 140 may be configured to be positionable alongside such body tissue.

The electrode array 140 may be implanted using any of a number of methods (e.g., a laminectomy procedure) well known to those of skill in the art. By way of a non-limiting example, the electrodes 142 may be implanted epidurally along the spinal cord 110 (see FIG. 1). The electrodes 142 may be positioned at one or more of a lumbosacral region, a cervical region, and a thoracic region of the spinal cord 110 (see FIG. 1). In the embodiment illustrated, the electrodes 142 are positioned distal to the lesion 112 (see FIG. 1) relative to the brain 108 (see FIG. 1). In other words, the electrodes 142 are positioned farther from the brain 108 than the lesion 112.

The one or more leads 130 illustrated include electrically conductive elements. In some embodiments, the one or more leads 130 include an electrically conductive element for each of the traces 144 of the electrode array 140. By way of another non-limiting example, in some embodiments, the one or more leads 130 include an electrically conductive element for each of the electrodes 142 of the electrode array 140. The one or more leads 130 of the assembly 100 connect the neurostimulator device 120 to the traces 144 of the electrode array 140, which are each connected to one of the electrodes 142. Thus, a signal generated by the neurostimulator device 120 is transmitted via the one or more leads 130 to selected ones of the traces 144, which transmit the signal to selected ones of the electrodes 142, which in turn deliver the stimulation to the body tissue in contact with the electrically conductive contacts (not shown) of the electrodes 142. The one or more leads 130 may vary in length. The electrically conductive elements may be constructed using a biocompatible substantially electrically conductive material (such platinum, Ag/AgCl, and the like), embedded in or surrounded by a biocompatible substantially electrically non-conductive (or insulating) material (e.g., flexible parylene). Optionally, the one or more leads 130 may include one or more connectors 132 and 134. In the embodiment illustrated, the connector 132 is used to connect the one or more leads 130 to the electrode array 140 and the connector 134 is used to connect the one or more leads 130 to the neurostimulator device 220.

Prior art epidural stimulating impulse generators (e.g., of the type designed for applications like back pain relief) cannot generate a complex pattern of stimulating signals needed to produce improved neurological function (e.g., stepping, standing, arm movement, and the like after a severe SCI or/and occurrence of a neuromotor disorders). For example, to recover stepping, an alternating spatiotemporal electric field having oscillations that peak over the right side of the spinal cord 110 (e.g., in the lumbosacral region) during a right leg swing phase, and oscillations that peak over the left side of the spinal cord 110 (e.g., in the lumbosacral region) during the left swing phase may be used. By way of another example, to recover independent standing, a rostral-caudal gradient in both electrode voltage and electrode stimulation frequency may be used. Rostral is nearer the brain 108 and caudal farther from the brain 108. Prior art stimulators are simply not configured to deliver such complex stimulation patterns.

Prior art epidural stimulating impulse generators have other limitations that limit their ability to help patients recover functionality lost as a result of the neurologically derived paralysis. For example, typical prior art stimulators deliver stimulation having the same amplitude to all active electrodes. Some prior art stimulators are configured to deliver stimulation having different amplitudes to four different groups of electrodes. Further, typical prior art stimulators deliver stimulation having the same frequency to all channels (or electrodes). Some prior art stimulators are configured to deliver stimulation having different frequencies to four groups of channels (or electrodes). Additionally, typical prior art stimulators deliver stimulation having the same pulse width to all of the channels (or electrodes). Further, typical prior art stimulators lack the ability to generate non-pulse waveforms.

Figure 4A:
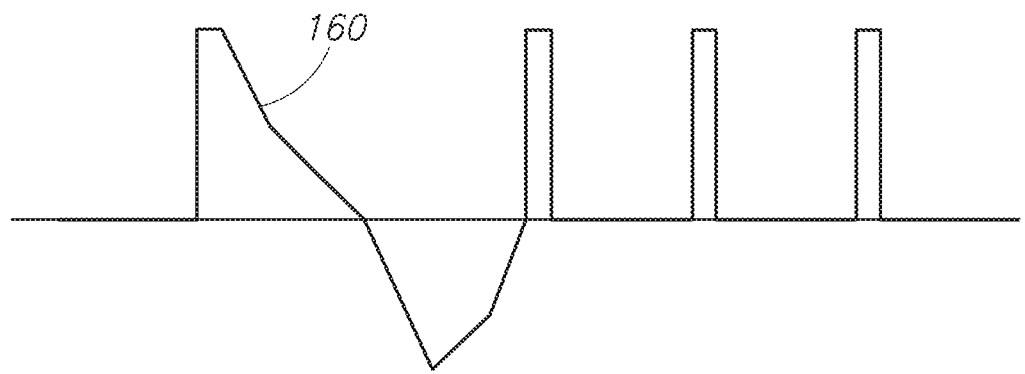
FIGS. 4A and 4B are illustrations of waveforms that may be generated by the neurostimulator device of the implantable assembly of FIG. 1.
Figure 4B:
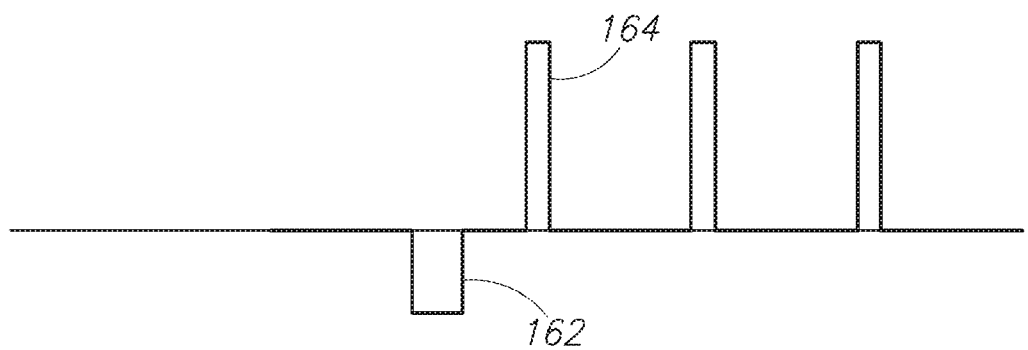

To achieve improved neurological function (e.g., stepping, standing, arm movement, and the like), a more complex waveform than the type generated by prior art stimulators must be delivered to one or more target locations. For example, it is known that non-rectangular waveforms (e.g., waveform 160 illustrated in FIG. 4A) and small "prepulses" (e.g., prepulse 162 illustrated in FIG. 4B) having a different amplitude and pulse width than the main "driving" pulse (e.g., driving pulse 164 illustrated in FIG. 4B) may be used to selectively recruit neurons with different fiber diameters and different electrical properties. Z.-P. Fang and J. T. Mortimer, "Selective Activation of Small Motor Axons by Quasitrapezoidal Current Pulses," *IEEE Trans. Biomedical Engineering*, 38(2):168-174, February 1991; and W. M. Grill and J. T. Mortimer, "Inversion of the Current-Distance Relationship by Transient Depolarization," *IEEE Trans. Biomedical Engineering*, 44(1):1-9, January 1997. Thus, these waveforms may be used to selectively recruit different parts of one or more sensory/motor circuits (e.g., activate different spinal circuits) as needed to achieve different therapeutic goals.

To achieve improved neurological function (e.g., stepping, standing, arm movement, and the like), the timing of the onset of electrical stimulation must be carefully controlled. For example, the spatio-temporal characteristics of the stimulating voltage fields needed for stepping require the ability to specify and control the phase shift (the exact timing of the onset of the stimulating waveform) between the electrodes 142, across the entire electrode array 140. Prior art stimulators lack this ability.

The neurostimulator device 120 is configured to generate complex types and patterns of electrical stimulation that achieve improved neurological function. In other words, the neurostimulator device 120 is configured to generate (and deliver to the electrode array 140) one or more "complex stimulation patterns." A complex stimulation pattern has at least the following properties:

1. a type of stimulation to apply to each of the electrodes 142 (which may include the application of no stimulation to one or more selected electrodes 142, if appropriate), the type of stimulation is defined by stimulation type parameters that include waveform shape, amplitude, waveform period, waveform frequency, and the like, the electrodes 142 being individually addressable;
2. stimulation timing that indicates when stimulation is to be applied to each of the electrodes 142 (which defines a sequence for applying stimulation to the electrodes 142), stimulation timing is defined by timing parameters that include an onset of stimulation, relative delay between waveform onset on different electrodes, a duration during which stimulation is delivered, a duration during which no stimulation is delivered, and the like; and
3. transition parameters that define how one waveform may be smoothly adapted over time to change (or morph) into a different waveform. Such smooth changes between waveform patterns may be helpful for enabling complex motor function, such as the transition from sitting to standing.

Together the stimulation type parameters, timing parameters, and transition parameters are "stimulation parameters" that define the complex stimulation pattern. The neurostimulator device 120 delivers the complex stimulation pattern to the electrode array 140. Thus, the electrode array 140 is configured such that which of the electrodes 142 will receive stimulation may be selected. In particular embodiments, the electrodes 142 are individually addressable by the neurostimulator device 120. Further, the neurostimulator device 120 may also be configured such that the frequency, waveform width (or period), and/or amplitude of the stimulation delivered to each of the selected ones of the electrodes 142 may also be adjustable. The complex stimulation pattern may remain constant, repeat, or change over time.

The configurability of the complex stimulation patterns delivered by the neurostimulator device 120 (by changing the stimulation parameters) enables the identification of effective complex stimulation patterns and the adjustment of the complex stimulation patterns to correct for migration and/or initial surgical misalignment. The neurostimulator device 120 may be configured to deliver a plurality of different complex stimulation patterns to the electrodes 142.

The neurostimulator device 120 is programmable (e.g., by the subject 102 or a physician). The neurostimulator device 120 may be programmed with stimulation parameters and/or control parameters configured to deliver a complex stimulation pattern that is safe, efficacious, and/or selected to target specific body tissue. Further, stimulation parameters and/or control parameters may be customized for each patient (e.g., based on response to pre-surgical (implant) evaluation and testing). The neurostimulator device 120 may have a variable activation control for providing a complex stimulation pattern either intermittently or continuously, and allowing for adjustments to frequency, waveform width, amplitude, and duration. By generating such customizable stimulation, the neurostimulator device 120 may be used to (a) generate or maintain efficacious and/or optimal complex stimulation patterns, and/or (b) adjust the location of the application of stimulation (relative to the neural tissue) when the assembly 100 migrates and/or was misaligned during implantation.

The neurostimulator device 120 may be configured to store, send, and receive data. The data sent and received may be transmitted wirelessly (e.g., using current technology, such as Bluetooth, ZigBee, FCC-approved MICS medical transmission frequency bands, and the like) via a wireless connection 155 (see FIG. 2). The neurostimulator device 120 may be configured to be regulated automatically (e.g., configured for open loop and/or closed loop functionality). Further, the neurostimulator device 120 may be configured to record field potentials detected by the electrodes 142, such as somatosensory evoked potentials (SSEPs) generated by the dorsum of the spinal cord 110. The neurostimulator device 120 may be configured to be rechargeable.

Depending upon the implementation details, the neurostimulator device 120 may be configured with one or more of the following properties or features:

1. a form factor enabling the neurostimulator device 120 to implanted via a surgical procedure;
2. a power generator with rechargeable battery;
3. a secondary back up battery;
4. electronic and/or mechanical components encapsulated in a hermetic package made from one or more biocompatible materials;
5. programmable and autoregulatory;
6. ability to record field potentials;
7. ability to operate independently, or in a coordinated manner with other implanted or external devices; and
8. ability to send, store, and receive data via wireless technology.

Optionally, the neurostimulator device 120 may be connected to one or more sensors 188 (e.g., Electromyography ("EMG") sensors 190, joint angle (or flex) sensors 191, accelerometers 192, gyroscopic sensors, pressure sensors, flow sensors, load sensors, and the like) via connections 194 (e.g., wires, wireless connections, and the like). The connections (e.g., the connections 194) and sensors 188 may be implemented using external components and/or implanted components. In embodiments including the sensors 188, the neurostimulator device 120 may be configured to modify or adjust the complex stimulation pattern based on information received from the sensors 188 via the connections 194. The connections 194 may implemented using wired or wireless connections. Optionally, the neurostimulator device 120 may be connected to reference wires 196. In FIG. 2, one of the reference wires 196 is positioned near the shoulder, the other of the reference wires 196 is positioned in the lower back. However, this is not a requirement.

In embodiments in which the connections 194 are implemented using wires, optionally, the connections 194 may include one or more connectors 136 and 138. In the embodiment illustrated, the connector 136 is used to connect the connections 194 to the sensors 188 and the connector 138 is used to connect the connections 194 to the neurostimulator device 220.

By way of a non-limiting example for use with relatively large subjects (e.g., humans), the neurostimulator device 120 may be approximately 20 mm to approximately 25 mm wide, approximately 45 mm to approximately 55 mm long, and approximately 4 mm to approximately 6 mm thick. By way of another non-limiting example for use with relatively small subjects (e.g., rats), the neurostimulator device 120 may be approximately 3 mm to approximately 4 mm wide, approximately 20 mm to approximately 30 mm long, and approximately 2 mm to approximately 3 mm thick.

As previously mentioned, placement of the assembly 100 is subcutaneous. The electrodes 142 are positioned on or near a target area (e.g., distal the lesion 112 illustrated in FIG. 1). If the subject 102 (see FIG. 2) has a SCI, the electrode array 140 may be positioned along the spinal cord 110 in a target area that is just distal to a margin of the lesion 112. Thus, if the paralysis was caused by SCI at a first location along the spinal cord 110 (see FIG. 1), the electrodes 142 may be implanted (e.g., epidurally) at a second location below the first location along the spinal cord relative to the subject's brain 108. The electrodes 142 may be placed in or on the spinal cord 110 (see FIG. 1), one or more spinal nerves, one or more nerve roots, one or more peripheral nerves, the brain stem, and/or the brain 108 (see FIG. 1).

The complex stimulation pattern may include at least one of tonic stimulation and intermittent stimulation. The stimulation applied may be pulsed. The electrical stimulation may include simultaneous or sequential stimulation of different regions of the spinal cord 110, one or more spinal nerves, one or more nerve roots, one or more peripheral nerves, the brain stem, and/or the brain 108 (see FIG. 1). The complex stimulation pattern applied by the assembly 100 may be below the second stimulation threshold such that the at least one selected spinal circuit is at least partially activatable by the addition of neurological signals (e.g., neurological signals induced by physical training or neurological signals originating from the brain 108) generated by the subject 102 (see FIG. 2). By way of a non-limiting example, neurological signals generated by the subject 102 may be induced by subjecting the subject to physical activity or training (such as stepping on a treadmill 170 while suspended in a harness 172 or other support structure). The neurological signals generated by the subject 102 may be induced in a paralyzed portion of the subject 102. By way of another non-limiting example, the neurological signals generated by the subject 102 may include supraspinal signals (or neurological signals originating from the brain 108).

As mentioned above, the embodiment of the assembly 100 illustrated in FIG. 1 is configured for implantation in the subject 102 (see FIG. 2). However, through application of ordinary skill in the art to the present teachings, embodiments may be constructed for use with other subjects, such as other mammals, including rats. The assembly 100 may be configured for chronic implantation and use. For example, the assembly 100 may be used to stimulate one or more nerve roots, one or more nerves, the spinal cord 110 (see FIG. 1), the brain stem, and/or the brain over time.

The implantable assembly 100 (see FIG. 1) may be used with an external system 180 illustrated in FIG. 2. Turning to FIG. 2, the external system 180 includes an external control unit 150 that may be used program, gather data, and/or charge the neurostimulator device 120 (e.g., via a wireless connection 155). In the embodiment illustrated in FIG. 2, the external control unit 150 is configured to be handheld. Optionally, the external system 180 includes a computing device 152 described in detail below. The external control unit 150 may connected via a connection 154 (e.g., a USB connection, wireless connection, and the like) to an external computing device 152.

The computing device 152 may be connected to a network 156 (e.g., the Internet) and configured to send and receive information across the network to one or more remote computing devices (e.g., a remote computing device 157).

In embodiments in which the computing device 152 is implemented with a wireless communication interface, the external control unit 150 may be omitted and the computing device 152 may communicate instructions directly to the neurostimulator device 120 via the wireless connection 155. For example, the computing device 152 may be implemented as a cellular telephone, tablet computing device, and the like having a conventional wireless communication interface. In such embodiments, the computing device 152 may communicate instructions to the neurostimulator device 120 using a wireless communication protocol, such as Bluetooth. Further, the computing device 152 may receive data from the neurostimulator device 120 via the wireless connection 155. Instructions and data may be communicate to and received from the remote computing device 157 over the network 156. Thus, the remote computing device 157 may be used to remotely program the neurostimulator device 120 (via the computing device 152) over the network 156.

One or more external sensors 158 may be connected to the computing device 152 via (wired and/or wireless) connections 159. Further, a motion capture system 166 may be connected to the computing device 152. The external sensors 158 and/or motion capture system 166 may be used to gather data about the subject 102 for analysis by the computing device 152 and/or the neurostimulator device 120.

The external sensors 158 may include at least one of the following: foot pressure sensors, a foot force plate, in-shoe sensors, accelerometers, surface EMG sensors, gyroscopic sensors, and the like. The external sensors 158 may be attached to or positioned near the body of the subject 102.

The motion capture system 166 may include any conventional motion capture system (e.g. a video-based motion capture system) and the present teachings are not limited to use with any particular motion capture system.

First Embodiment

Figure 5:
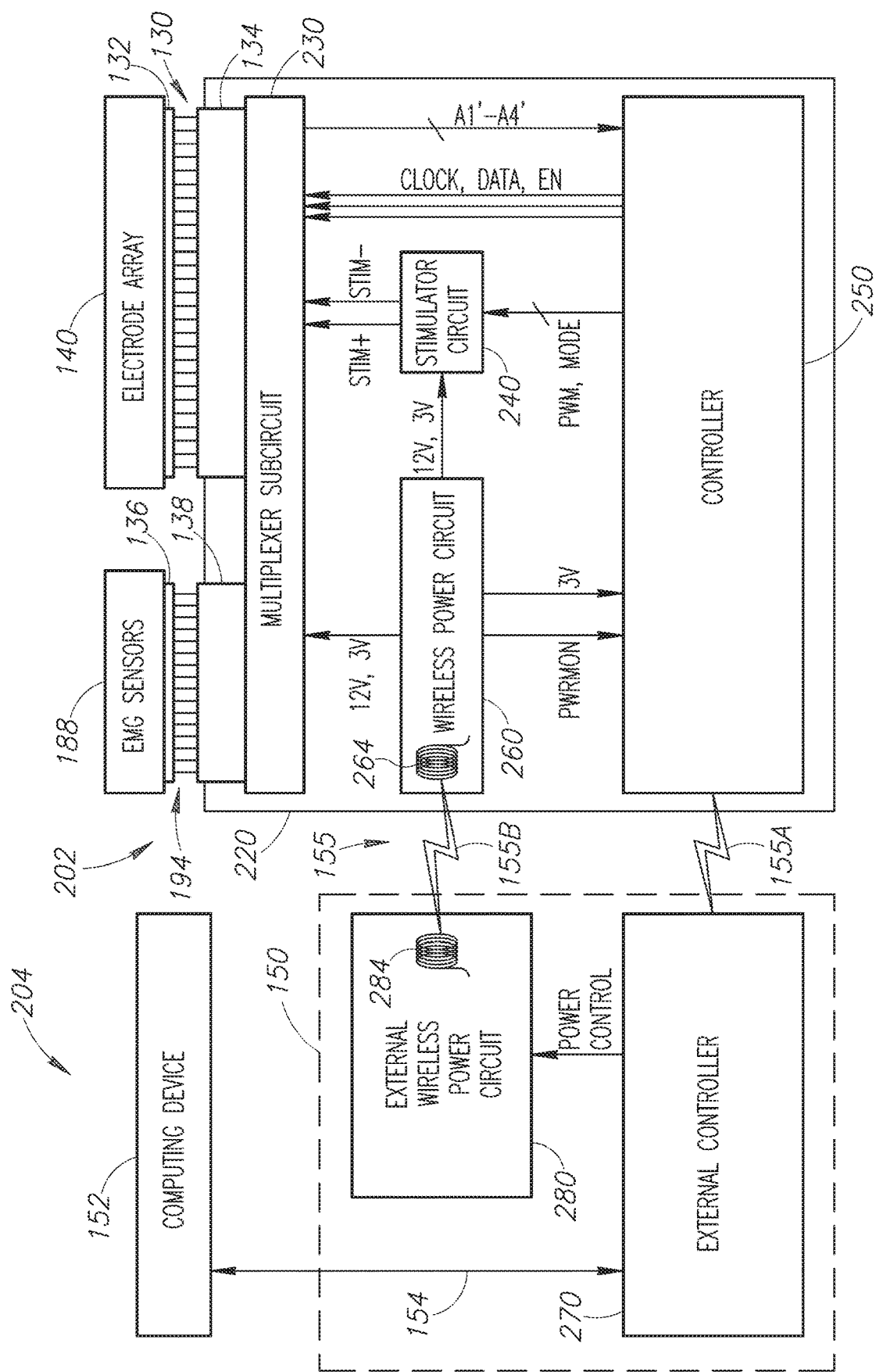
FIG. 5 is a block diagram of a first embodiment of an implantable assembly and an external system.

FIG. 5 is a block diagram of a first embodiment of a system 200. The system 200 includes an implantable assembly 202 substantially similar to the assembly 100 described above, and an external system 204 substantially similar to the external system 180 described above. Therefore, only components of the assembly 202 that differ from those of the assembly 100, and components of the external system 204 that differ from those of the external system 180 will be described in detail. For ease of illustration, like reference numerals have been used to identify like components in FIGS. 1-3 and 5.

The assembly 202 includes a neurostimulator device 220, the one or more leads 130, and the electrode array 140, and the connections 194. The assembly 202 may also include the reference wires 196 (see FIG. 2). By way of a non-limiting example, the assembly 202 may include the two reference wires illustrated in FIG. 2. In the embodiment illustrated, the connections 194 include sixteen wires, each connected to a different one of the sensors 188 (e.g., the EMG sensors 190). However, this is not a requirement and embodiments may be constructed using a different number of connections (e.g., wires), a different number of sensors, and/or different types of sensors without departing from the scope of the present teachings.

In the embodiment illustrated, the electrode array 140 includes the 27 electrodes A1-A9, B1-B9, and C1-C9. However, this is not a requirement and embodiments including different numbers of electrodes (e.g., 16 electrodes, 32 electrodes, 64 electrodes, 256 electrodes, etc.) are within the scope of the present teachings. Particular embodiments include at least 16 electrodes.

The neurostimulator device 220 is configured to send a stimulating signal (e.g., a "pulse") to any of the electrodes 142 in the electrode array 140. The neurostimulator device 220 is also configured to switch between different electrodes very rapidly. Thus, the neurostimulator device 220 can effectively send a predefined pattern of pulses to selected ones of the electrodes 142 in the electrode array 140. In some embodiments, the neurostimulator device 220 is configured to generate a wide variety of waveforms such that virtually any pulsed waveform can be generated. As mentioned above, the electrodes 142 may be arranged in more than four groups, each group including one or more of the electrodes. Further, an electrode may be included in more than one group. In groups including more than one electrode, the electrodes may be stimulated simultaneously.

The wireless connection 155 may be two components, a communication connection 155A and a power transfer connection 155B.

Depending upon the implementation details, the neurostimulator device 220 may be configured to deliver stimulation having the following properties:
1. A maximum voltage (e.g., a constant voltage mode) of about ±12 V;
2. A maximum stimulating current (e.g., a constant current mode) of about ±5 mA;
3. A maximum stimulation frequency of about 100 kHz;
4. A minimum pulse width of about 0.1 ms having a frequency as high as about 50 kHz;
5. A maximum recording bandwidth of about 60 kHz (−3 dB);
6. Digital to Analog converter ("DAC") resolution of about 7 bits to about 12 bits;
7. Configuration switch time of about 3 µs;
8. Ability to configure stimulation and deliver stimulation (e.g., a pulse) about 100 times per millisecond;
9. Simultaneously addressable electrodes (e.g., any pair of the electrodes 142 may be addressed with multiple groups (e.g., more than four groups) of electrodes being addressable (e.g., stimulated or recorded from) simultaneously);
10. Any of the electrodes 142, if not used for applying stimulation, can be selected as a differential pair of electrodes and used for recording;
11. A wireless data transfer rate of about 250 kBps (ISM band 915 MHz) across the communication connection 155A to send and/or receive data; and
12. A maximum power consumption of about 100 mW.

In the embodiment illustrated, the neurostimulator device 220 includes a multiplexer sub-circuit 230, a stimulator circuit 240, a controller 250 (connected to a controller circuit 252 illustrated in FIG. 8), and an optional wireless power circuit 260. The controller 250 sends three control signals Clock, Data, and EN to the multiplexer sub-circuit 230, and receives data A1'-A4' from the multiplexer sub-circuit 230. The stimulator circuit 240 provides a first stimulation signal STIM+ and a second stimulation signal STIM− to the multiplexer sub-circuit 230. The controller 250 sends control signals PWM and MODE to the stimulator circuit 240. The control signal MODE sent by the controller 250 to the stimulator circuit 240 instructs the stimulator circuit 240 to operate in either constant voltage mode or constant current mode. The control signal PWM sent by the controller 250 to the stimulator circuit 240 uses pulse-width modulation to control power sent by the stimulator circuit 240 to the multiplexer sub-circuit 230 as the first and second stimulation signals STIM+ and STIM−. Thus, the control signal PWM configures at least a portion of the complex stimulation pattern. However, the multiplexer sub-circuit 230 determines which of the electrodes 142 and/or connections 194 receives the stimulation. Therefore, the multiplexer sub-circuit 230 configures at least a portion of the complex stimulation pattern. However, both the stimulator circuit 240 and the multiplexer sub-circuit 230 configure the complex stimulation pattern based on instructions received from the controller 250.

The controller 250 is connected wirelessly to the external programming unit 150 via the communication connection 155A. The communication connection 155A may be configured to provide bi-directional wireless communication over which the controller 250 may receive system control commands and data from the external programming unit 150, as well as transmit status information and data to the external programming unit 150. In some embodiments, the communication connection 155A may include one or more analog communication channels, one or more digital communication channels, or a combination thereof.

The controller 250 receives power (e.g., 3V) from the wireless power circuit 260 and a power monitoring signal PWRMON from the wireless power circuit 260. The wireless power circuit 260 provides power (e.g., 12V and 3V) to the multiplexer sub-circuit 230. The wireless power circuit 260 also provides power (e.g., 12V and 3V) to the stimulator circuit 240. The wireless power circuit 260 receives power wirelessly from the external programming unit 150 via the power transfer connection 155B.

Figure 6A:
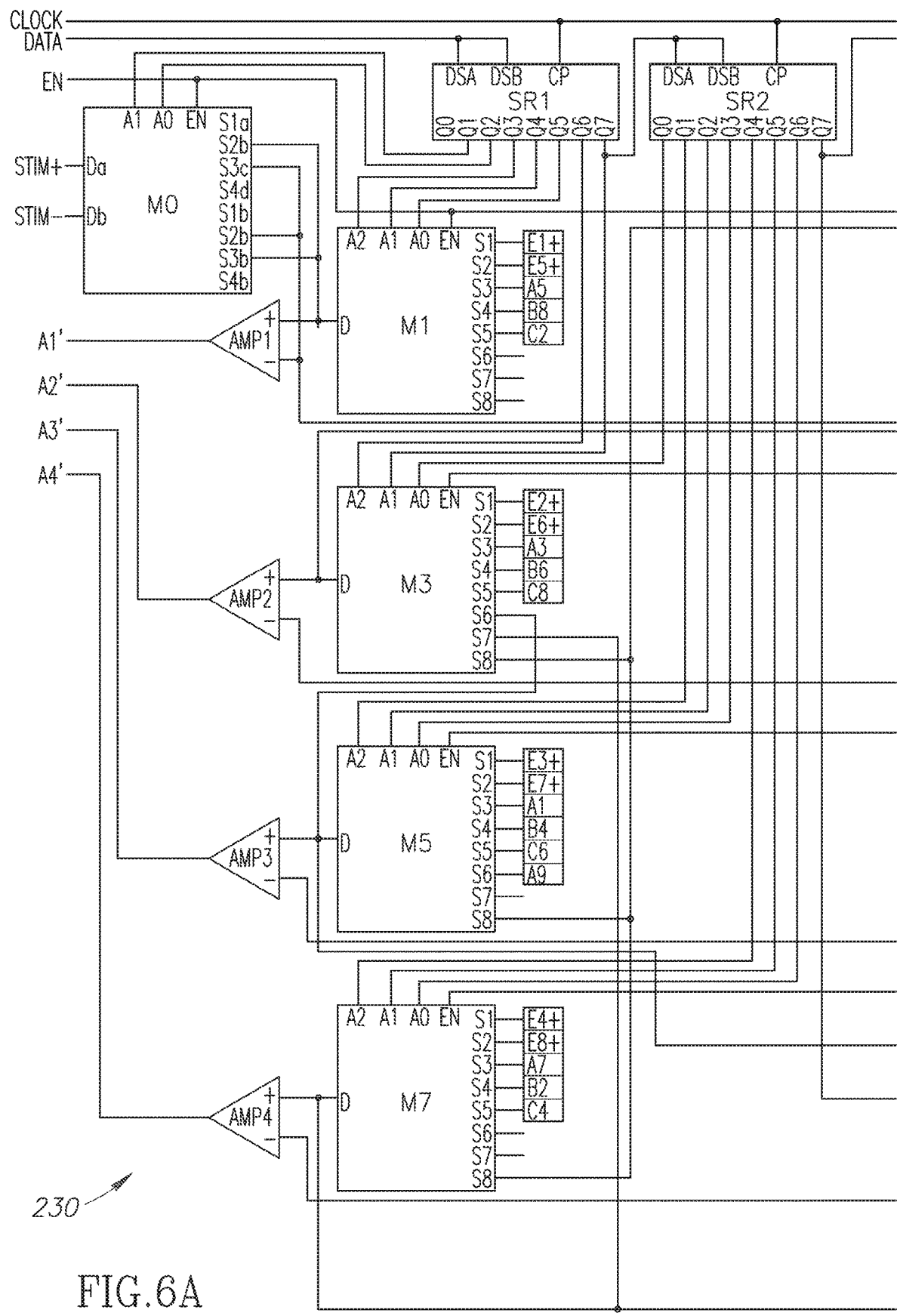
FIG. 6A is a leftmost portion of a circuit diagram of a multiplexer sub-circuit of a neurostimulator device of the implantable assembly of FIG. 5.
Figure 6B:
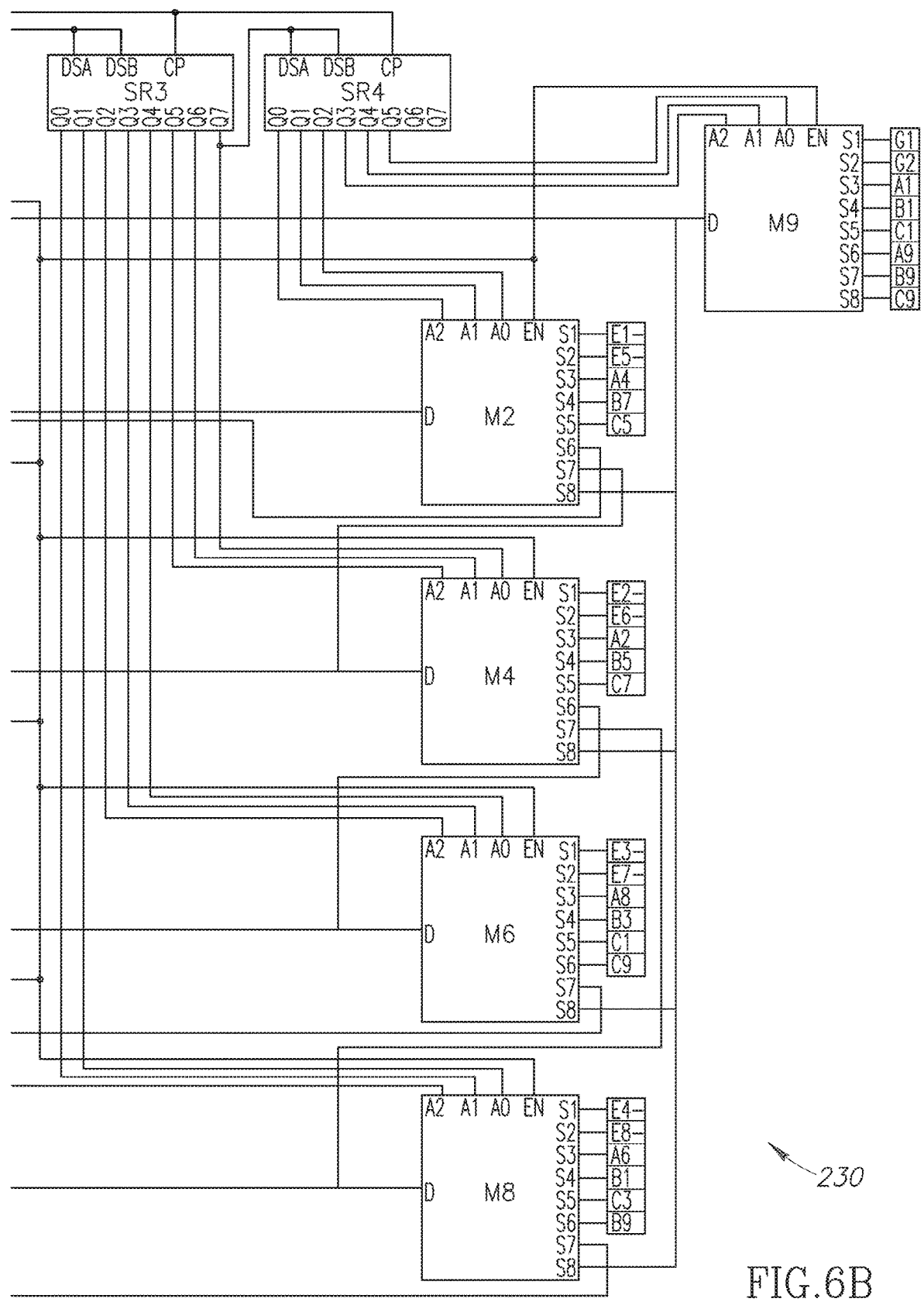
FIG. 6B is a rightmost portion of the circuit diagram of the multiplexer sub-circuit of the neurostimulator device of the implantable assembly of FIG. 5.

FIGS. 6A and 6B are a circuit diagram of an exemplary implementation of the multiplexer sub-circuit 230. FIG. 6A is a leftmost portion of the circuit diagram of the multiplexer sub-circuit 230, and FIG. 6B is a rightmost portion of the circuit diagram of the multiplexer sub-circuit 230. The circuit diagram of FIGS. 6A and 6B includes amplifiers AMP1-AMP4, shift registers SR1-SR4 (e.g., implemented using NXP Semiconductors 74HC164), and analog multiplexer chips M0-M9.

The amplifiers AMP1-AMP4 output the data A1'-A4', respectively. The amplifiers AMP1-AMP4 (e.g., Analog Devices AD8224) may be implemented as differential amplifiers with a gain set to 200. However, as is apparent to those of ordinary skill in the art, other gain values may be used. Further, the gains of the amplifiers AMP1-AMP4 may be readily changed by modifications to the components known to those of ordinary skill in the art.

The multiplexer sub-circuit 230 routes the first and second stimulation signals Stim+ and Stim− to the selected ones of the electrodes 142 and/or connections 194. The multiplexer sub-circuit 230 also routes signals received from selected ones of the electrodes 142 and/or connections 194 to the amplifiers AMP1-AMP4. Thus, the multiplexer sub-circuit 230 is configured to route signals between the stimulator circuit 240, the amplifiers AMP1-AMP4, the electrodes 142, and the connections 194.

The controller 250 sends a 30-bit serial data stream through the control signals Clock and Data to the multiplexer sub-circuit 230, which is fed into the shift registers SR1-SR4. The shift registers SR1-SR4 in turn control the analog multiplexer chips M0-M9, which are enabled by the control signal EN.

The multiplexer chip M0 has inputs "Da" and "Db" for receiving the first and second stimulation signals STIM+ and STIM−, respectively, from the controller 250. The multiplexer chip M0 is used to disconnect one or more of the electrodes 142 and/or one or more of the sensors 188 (e.g., the EMG sensors 190) during recording of signals detected by the disconnect component(s). The multiplexer chip M0 is also used to select a polarity (or tristate) for each of the electrodes 142 when stimulation is applied. The multiplexer chip M0 may be implemented as a 2×(4:1) multiplexer (e.g., Analog Devices ADG1209).

The multiplexer chips M1-M9 are interconnected to connect almost any pair of the electrodes 142 or connections 194 to the amplifier AMP1 and the inputs "Da" and "Db" (which receive the first and second stimulation signals STIM+ and STIM−, respectively) of multiplexer chip M0. The multiplexer chips M1-M9 may each be implemented using an 8:1 multiplexer (e.g., Analog Devices ADG1208).

With respect to the multiplexer chips M1-M9, a label in each rectangular tag in the circuit diagram identifies a connection to one of the electrodes 142 or connections 194. Each label in a rectangular tag starting with the letter "E" identifies a connection to one of the connections 194 connected to one of the sensors 188 (e.g., one of the EMG sensors 190). For example, the label "E1+" adjacent multiplexer chip M1 identifies a connection to a first wire, and the label "E1−" adjacent multiplexer chip M2 identifies a connection to a second wire. Together, the labels "E1+" and "E1−" identify connections a first pair of the connections 194.

The labels "G1" and "G2" adjacent multiplexer chip M9 identify connections to the reference wires 196 (see FIG. 2).

Each label in a rectangular tag starting with a letter other than the letter "E" or the letter "G" identifies a connection to one of the electrodes 142. For example, the label "A3" refers to a connection to the electrode A3 (see FIG. 3) in column A and row 3 (where column A is leftmost, column B is in the middle, column C is rightmost, row 1 is rostral, and row 9 is caudal).

Optionally, some key electrodes may have more than one connection to the multiplexer sub-circuit 230. For example, the electrodes A1, B1, C1, A9, B9, and C9 are each identified by more than one label.

The multiplexer sub-circuit 230 is designed to operate in four modes. In a first mode, the multiplexer sub-circuit 230 is configured to select an individual electrode to which to apply a monopolar stimulating pulse. In a second mode, the multiplexer sub-circuit 230 is configured to select a pair of the electrodes 142 to stimulate in a bipolar fashion. In a third mode, the multiplexer sub-circuit 230 is configured to select a single electrode from which to record, with the recorded waveform referenced to a ground signal. In a fourth mode, the multiplexer sub-circuit 230 is configured to select a pair of the electrodes 142 from which to record in a differential fashion.

As mentioned above, the neurostimulator device 220 can provide selective stimulation to any of the electrodes 142. The multiplexer sub-circuit 230 is configured to route stimulation between almost any pair of the electrodes 142 or the connections 194. For example, the electrode A1 may be the anode and the electrode B6 the cathode.

The multiplexer sub-circuit 230 is configured route signals received from the connections 194 to the amplifiers AMP1-AMP4 and to the controller 250 (in data A1'-A4') for recording thereby. Similarly, the multiplexer sub-circuit 230 is configured route signals received from the electrodes 142 to the amplifiers AMP1-AMP4 and to the controller 250 (in data A1'-A4') for recording thereby. By way of a non-limiting example, the multiplexer sub-circuit 230 may be configured route signals received from four electrodes positioned in the same column (e.g. electrodes A1, A3, A5, and A7) and signals received from a fifth electrode (e.g., electrode A9) positioned in the same column to the controller 250 (in data A1'-A4' output by the amplifiers AMP1-AMP4) so that a differential signal received from the first four relative to the fifth may be recorded by the controller 250 for each pair of electrodes (e.g., a first pair including electrodes A1 and A9, a second pair including electrodes A3 and A9, a third pair including electrodes A5 and A9, and a fourth pair including electrodes A7 and A9).

As mentioned above, the multiplexer sub-circuit 230 receives power (e.g., 12V and 3V) from the wireless power circuit 260. For ease of illustration, power lines providing this power to the multiplexer sub-circuit 230 have been omitted. The power lines may be implemented using one line having a voltage of about +12V, one line having a voltage of about +2V to about +6V (e.g., +3V), and one ground line.

The multiplexer sub-circuit 230 may be configured to change configurations in less than one microsecond in embodiments in which the control signals Clock and Data are fast enough. This allows the first and second stimulation signals Stim+ and Stim−(received from the stimulator circuit 240) to be delivered in short pulses to selected ones of the electrodes 142 in about one millisecond and also allows the amplifiers AMP1-AMP4 to rapidly switch input signals so the controller 250 may effectively record from 8 or 16 signals (instead of only four) within as little as about 20 microseconds. In some embodiments, the controller 250 may effectively record from 8 or 16 signals (instead of only four) within as little as 5 microseconds.

Figure 7:
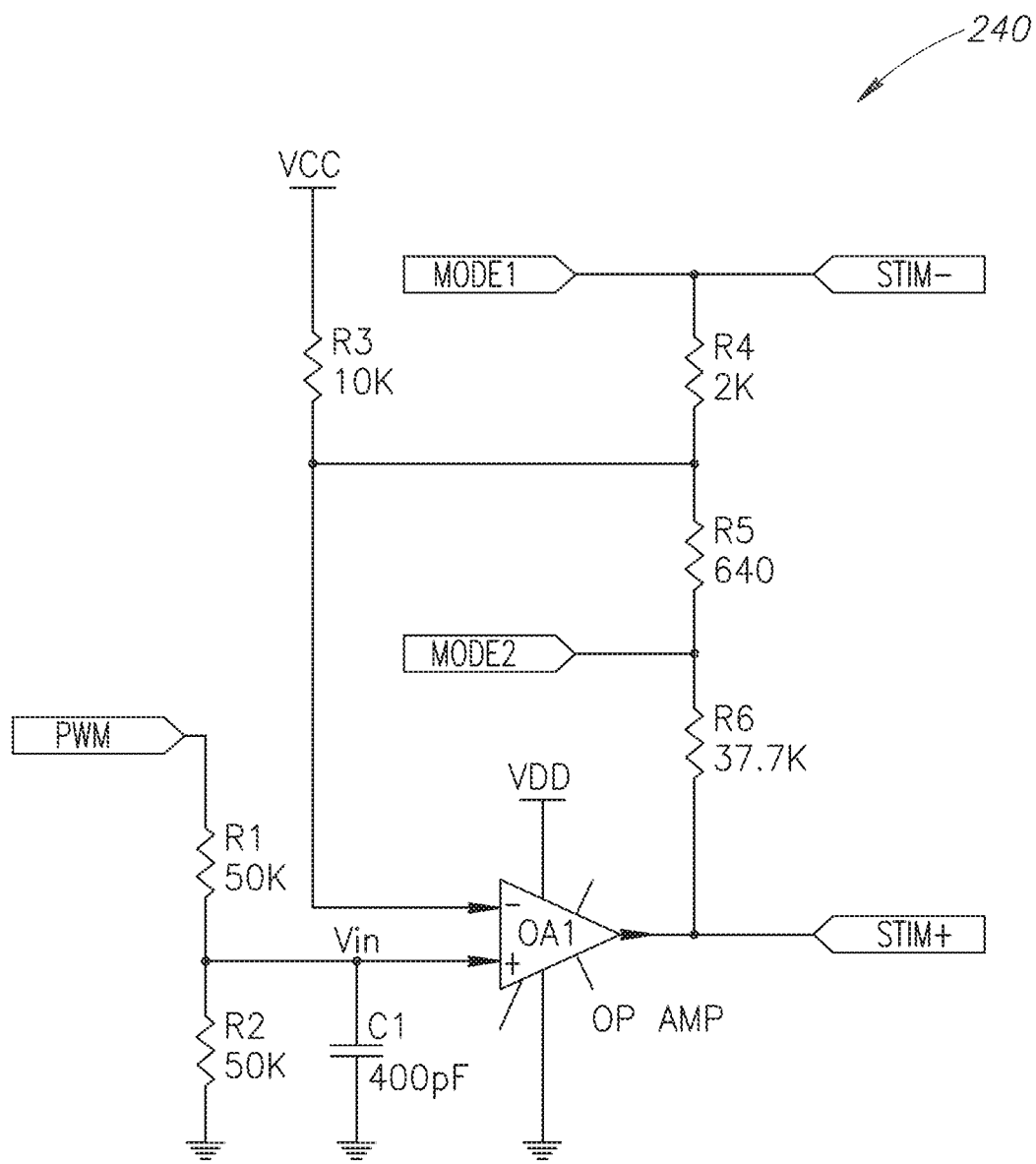
FIG. 7 is a circuit diagram of a stimulator circuit of the neurostimulator device of the implantable assembly of FIG. 5.

FIG. 7 is a circuit diagram of an exemplary implementation of the stimulator circuit 240. As mentioned above, the stimulator circuit 240 is configured to selectively operate in two modes: constant voltage mode and constant current mode. In FIG. 7, labels "Mode1" and "Mode2" identify connections to pins "P1_0" and "P1_1," respectively, of the controller 250 (see FIG. 8). When pin "P1_0" (connected to the connection labeled "Mode1") is set to ground and pin "P1_1" (connected to the connection labeled "Mode2") is high impedance, the stimulator circuit 240 is in constant voltage mode. When pin "P1_1" (connected to the connection labeled "Mode2") is set to ground and pin "P1_0" (connected to the connection labeled "Mode1") is high impedance, the stimulator circuit 240 is in constant current mode.

Figure 8:
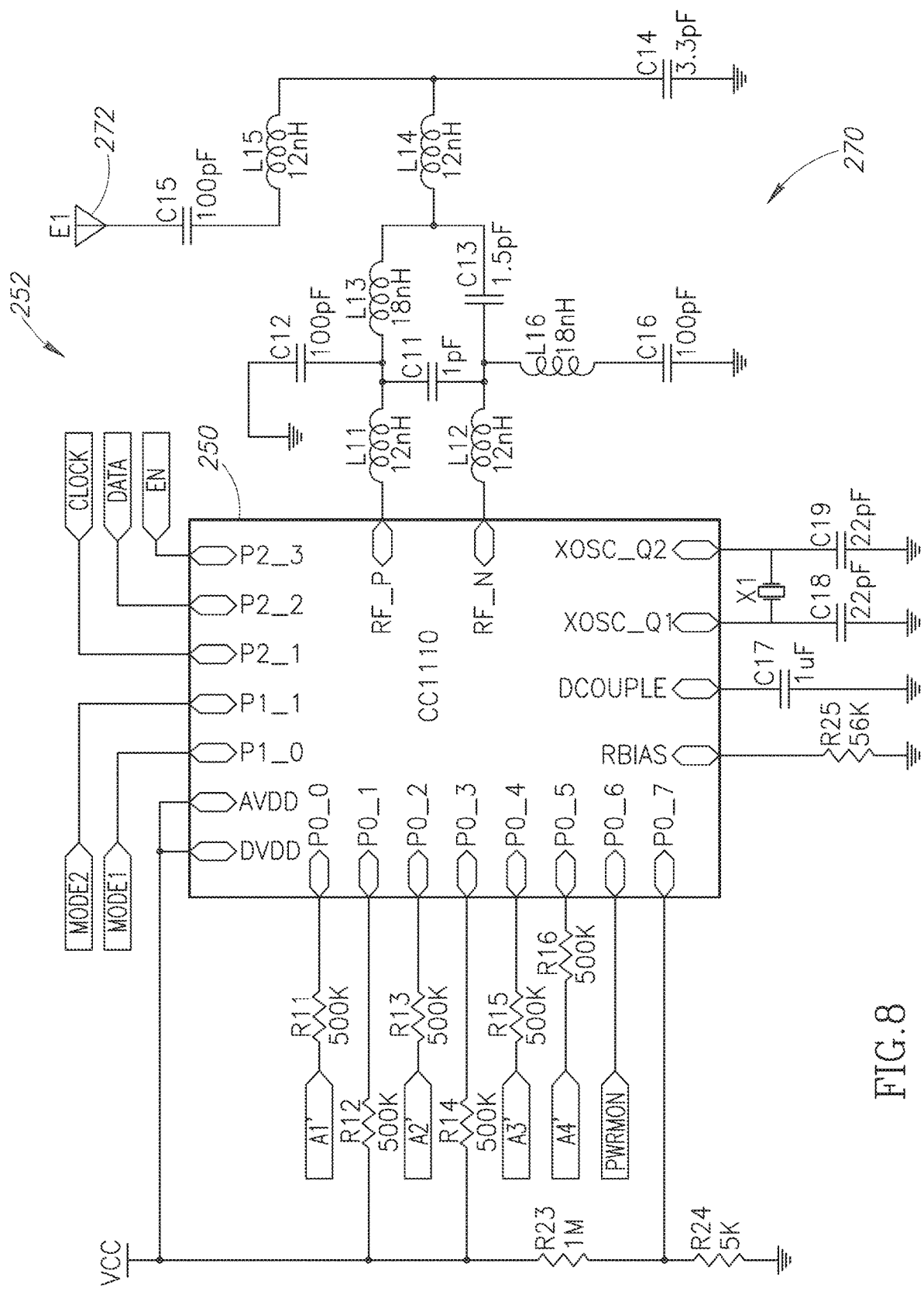
FIG. 8 is a circuit diagram of a controller circuit of the neurostimulator device of the implantable assembly of FIG. 5.

FIG. 8 is a circuit diagram of an exemplary implementation of a controller circuit 252 that includes the controller 250 and its surrounding circuitry. The controller 250 controls the multiplexer sub-circuit 230, records amplified signals received (in the data A1'-A4') from the multiplexer sub-circuit 230, and monitors wireless power (using the power monitoring signal PWRMON received from the wireless power circuit 260). The controller 250 also communicates with an external controller 270. In the embodiment illustrated, the controller 250 has been implemented using a Texas Instruments CC1110. However, through application of ordinary skill to the present teachings, embodiments may be constructed in which the controller 250 is implemented using a different microcontroller, a microprocessor, a Field Programmable Gate Array ("FPGA"), a Digital Signal Processing ("DSP") engine, a combination thereof, and the like.

It may be desirable to record signals (e.g., Motor Evoked Potentials (MEPs)) received from the electrode array 140. For example, recorded MEPs can help assess the health and state of the spinal cord 110, and may be used to monitor the rate and type of recovery of spinal cord function under long-term epidural stimulation. Therefore, in some embodiments, the controller circuit 252 is configured to record voltages and currents received from the electrode array 140 when it is not stimulated. In such embodiments, the controller circuit 252 is also configured to transmit the recorded data over the communication connection 155A (e.g., in "real time") to the external programming unit 150. In the embodiment illustrated, the controller circuit 252 includes an antenna 272 configured to communicate with the external controller 270. The controller circuit 252 may be configured to coordinate stimulating (signal sending) and reading (signal receiving) cycles with respect to the electrode array 140.

With respect to controlling the state of the implanted neurostimulator device 220, the controller circuit 252 may be configured to measure (and/or control) the exact timing of the onset of stimulation. The controller circuit 252 may be configured to reset or stop stimulation at a desired time. The controller circuit 252 may be configured to transition smoothly between successive stimulation (e.g., pulses) and successive stimulation patterns.

With respect to patient monitoring and safety, the controller circuit 252 may be configured to monitor electrode impedance, and impedance at the electrode/tissue interface. Of particular concern is impedance at relatively low frequencies (e.g., 10-1000 Hz). The controller circuit 252 may be configured to limit current and voltage. Further, the controller circuit 252 may be configured to trigger an alarm (or send an alarm message to the computing device 152) when voltage or current limits are exceeded. Optionally, the neurostimulator device 220 may shut down or power down if an unsafe condition is detected.

The external controller 270 may be used to program the controller 250. The external controller 270 may be a component of the external control unit 150 (see FIG. 2). The external controller 270 may be implemented using a Texas Instruments CC1111. The external controller 270 may relay information to and from the computing device 152 through the connection 154 (e.g., a USB connection, and/or a wireless connection).

The computing device 152 may be configured to control data streams to be sent to the neurostimulator device 220. The computing device 152 may interpret data streams received from the neurostimulator device 220. In some implementations, the computing device 152 is configured to provide a graphical user interface for communicating with the neurostimulator device 220. The user interface may be used to program the neurostimulator device 220 to deliver particular stimulation. For example, the user interface may be used to queue up a particular sequence of stimuli. Alternatively, the computing device 152 may execute a method (e.g., a machine learning method described below) configured to determine stimulation parameters. In some embodiments, the user interface may be used to configure the method performed by the computing device 152. The user interface may be used to transfer information recorded by the neurostimulator device 220 to the computing device 152 for storage and/or analysis thereby. The user interface may be used to display information indicating an internal system state (such the current selection of stimulation parameters values) and/or mode of operation (e.g., constant voltage mode, constant current mode, and the like).

Figure 9:
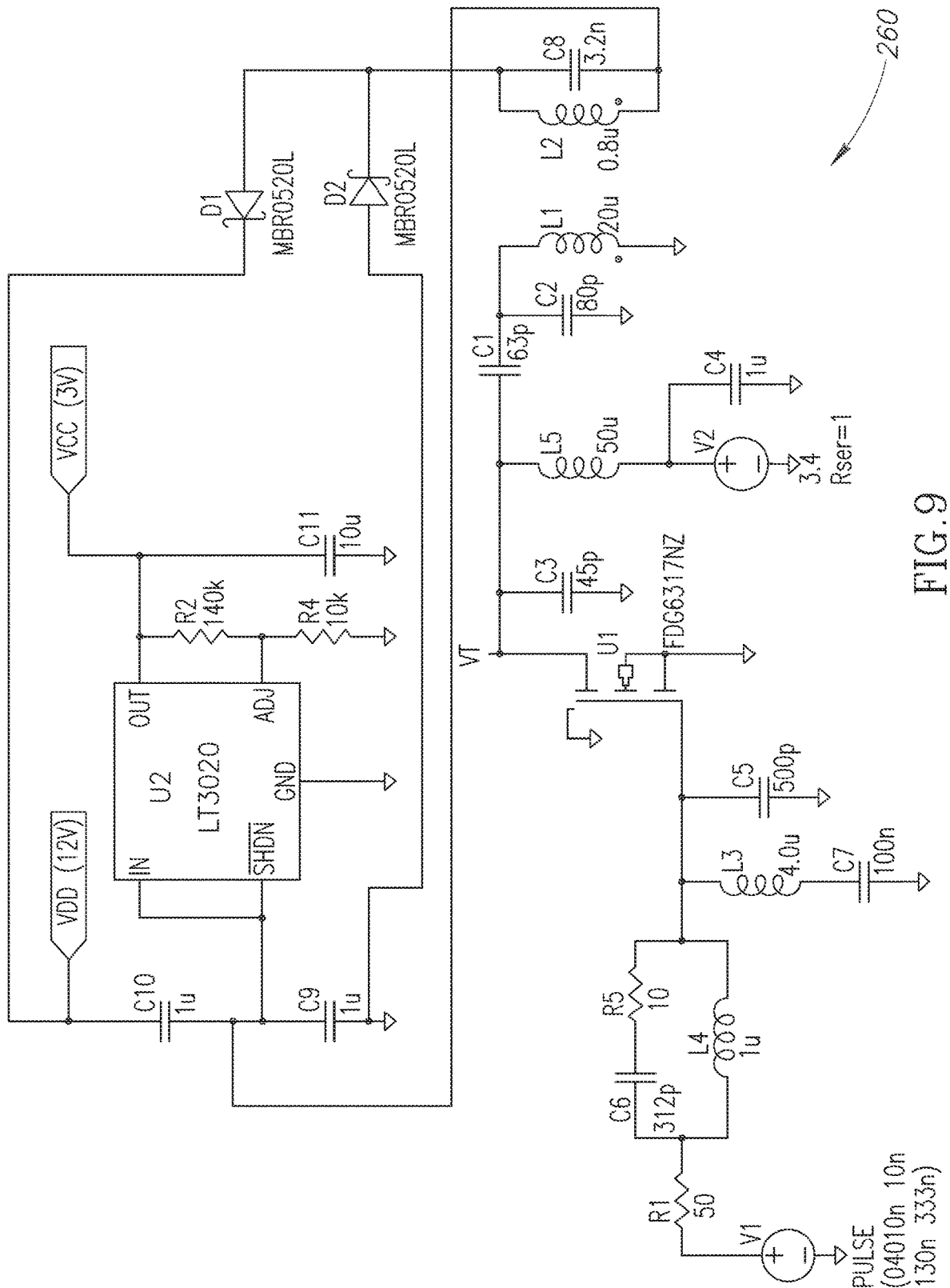
FIG. 9 is a circuit diagram of a wireless power circuit of the neurostimulator device of the implantable assembly of FIG. 5.

FIG. 9 is a circuit diagram of an exemplary implementation of the optional wireless power circuit 260. The wireless power circuit 260 is configured to receive power wirelessly from an external wireless power circuit 280. The wireless power circuit 260 may supply both about 3V DC (output VCC) and about 12V DC (output VDD). As mentioned above, the output VCC is connected to the multiplexer sub-circuit 230, the stimulator circuit 240, and the controller 250, and the output VDD is connected to the multiplexer sub-circuit 230 and the stimulator circuit 240.

The external wireless power circuit 280 may be a component of the external control unit 150 (see FIG. 2). The external wireless power circuit 280 may be implemented using a Class E amplifier and configured to provide variable output. In the embodiment illustrated, the external wireless power circuit 280 provides power to the wireless power circuit 260 via inductive coupling over the power transfer connection 155B. The wireless power circuit 260 may include a radio frequency ("RF") charging coil 264 and the external wireless power circuit 280 includes an RF charging coil 284 configured to transfer power (e.g., inductively) to the RF charging coil 264. Optionally, communication channels may be multiplexed on the wireless transmission.

The wireless power circuit 260 may be connected to one or more rechargeable batteries (not shown) that are chargeable using power received from the external wireless power circuit 280. The batteries may be implemented using rechargeable multi-cell Lithium Ion Polymer batteries.

Second Embodiment

Figure 10:
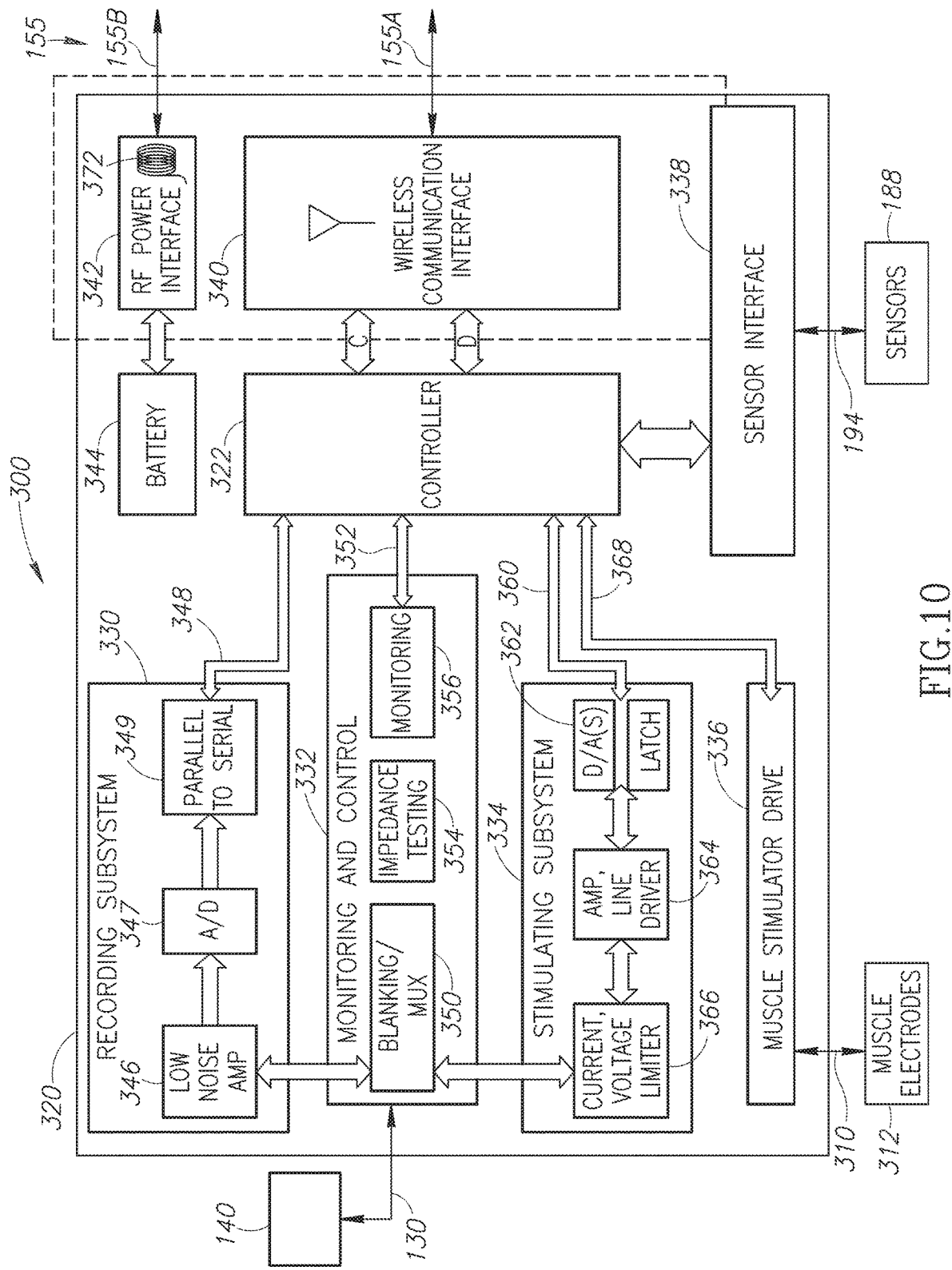
FIG. 10 is a block diagram of a second embodiment of an implantable assembly.

FIG. 10 is a block diagram of an implantable assembly 300. For ease of illustration, like reference numerals have been used to identify like components in FIGS. 1-3, 5, and 10. The assembly 300 may be configured to communicate with the external controller 270 via the communication connection 155A. Optionally, the assembly 300 may receive power wirelessly from the external wireless power circuit 280 via inductive coupling over the power transfer connection 155B.

In addition to providing complex stimulation patterns to body tissue (e.g., neurological tissue), the assembly 300 is configured to also provide electrical stimulation directly to muscles (not shown) that will cause the muscle to move (e.g., contract) to thereby augment the improved neurological function provided by the complex stimulation patterns alone. The assembly 300 is configured to provide one or more complex stimulation patterns to 16 or more individually addressable electrodes for purposes of providing improved neurological function (e.g., improved mobility recovery after SCI).

The assembly 300 includes a neurostimulator device 320, the one or more leads 130, and the electrode array 140, the connections 194 (connected to the sensors 188), and connections 310 (e.g., wires, wireless connections, and the like) to (implanted and/or external) muscle electrodes 312. The assembly 300 may also include the reference wires 196 (see FIG. 2). By way of a non-limiting example, the assembly 300 may include the two reference wires illustrated in FIG. 2. In the embodiment illustrated, the connections 194 include sixteen wires, each connected to a different one of the sensors 188 (e.g., the EMG sensors 190). However, this is not a requirement and embodiments may be constructed using a different number of wires, a different number of EMG sensors, and/or different types of sensors without departing from the scope of the present teachings.

The neurostimulator device 320 includes a controller 322, a recording subsystem 330, a monitor and control subsystem 332, a stimulating subsystem 334, a muscle stimulator drive 336, a sensor interface 338, a wireless communication interface 340, an RF power interface 342, and at least one power source 344 (e.g., a rechargeable battery). In the embodiment illustrated, the controller 322 has been implemented using a microcontroller (e.g., a Texas Instruments CC1110). However, through application of ordinary skill to the present teachings, embodiments may be constructed in which the controller 250 is implemented using a microprocessor, FPGA, DSP engine, a combination thereof, and the like.

The recording subsystem 330 is configured to record electrical signals received from one or more of the electrodes 142 in the electrode array 140. The electrodes used to record may be the same electrodes used to provide the complex stimulation pattern, or different electrodes specialized for recording. The recording subsystem 330 may be connected (directly or otherwise) to one or more of the leads 130. In the embodiment illustrated, the recording subsystem 330 is connected to the leads 130 via the monitor and control subsystem 332.

The recording subsystem 330 includes one or more amplifiers 346. In the embodiment illustrated, the amplifiers 346 are implemented as low noise amplifiers ("LNAs") with programmable gain.

The monitor and control subsystem 332 illustrated includes a blanking circuit 350 that is connected directly to the leads 130. The blanking circuit 350 is configured to disconnect the recording subsystem 330 (which is connected thereto) from the leads 130 when the complex stimulation pattern is applied to the electrodes 142 to avoid damaging the amplifiers 346. Bidirectional control and status lines (not shown) extending between the blanking circuit 350 and the controller 340 control the behavior of the blanking circuit 350.

The monitor and control subsystem 332 monitors the overall activity of the neurostimulator device 320, as well as the functionality (e.g., operability) of the electrode array 140. The monitor and control subsystem 332 is connected to the CPU by bidirectional digital and analog signal and control lines 352. In some embodiments, the monitor and control subsystem 332 includes a circuit 354 configured to monitor electrode impedance. Optionally, a multiplexer (not shown) may be connected to the leads 130, allowing the monitor and control subsystem 332 to selectively interrogate the signal received from each electrode. The output of the multiplexer (not shown) is connected to an A/D circuit (not shown), so that a signal received from a selected one of the electrodes 142 can be digitized, and transmitted to the controller 322 to assess the functionality of the stimulating circuitry. The monitor and control subsystem 332 may include circuitry 356 configured to assess the functionality (e.g., operability) of the power source 344.

The amplifiers 346 receive signals from the leads 130 when the blanking circuit 350 is in the off state. In some embodiments, a different one of the amplifiers 346 is connected to each different one of the leads 130. In other embodiments, the blanking circuit 350 includes or connected to a multiplexing circuit having an input is connected to the leads 130 and the output of the blanking system 350. In such embodiments, the multiplexing circuit routes an electrode signal (selected by the controller 322) to a single one of the amplifiers 346. The amplifiers 346 are connected to the controller 322 via bidirectional control and status lines (not shown) that allow the controller 322 to control the gain and behavior of the amplifiers 346.

The recording subsystem 330 includes an analog-to-digital ("A/D") circuit 347 that digitizes the output(s) received from the amplifiers 346. In some embodiments, a separate A/D circuit is dedicated to the output of each amplifiers 346. In other embodiments, a multiplexing circuit (not shown) routes the output of a selected one of the amplifiers 346 to a single A/D circuit. The output of the A/D circuit 347 is connected via a serial or parallel digital bus 348 to the controller 322. In the embodiment illustrated, the recording subsystem 330 includes a parallel to serial circuit 349 that serializes the output received from the A/D circuit 347 for transmission on the bus 348. Control and status lines (not shown) connect the A/D circuit 347 to the controller 322, allowing the controller 322 to control the timing and behavior of the A/D circuit 347.

The stimulating subsystem 334 will be described as delivering complex stimulation patterns over channels. Each channel corresponds to one of the electrodes 142. Stimulation delivered over a channel is applied to the corresponding one of the electrodes 142. Similarly, stimulation received from one of the electrodes 142 may be received over the corresponding channel. However, in some embodiments, two or more electrodes may be physically connected to the same channel so their operation is governed by a single channel.

The stimulating subsystem 334 is configured to generate complex stimulation patterns, which as explained above include complex waveforms (either in voltage or current mode), and deliver the stimulation on each of one or more of the channels. The stimulating subsystem 334 is connected to the controller 322 by multiple bidirectional lines 360 over which the stimulating subsystem 334 receives commands and stimulating waveform information. The stimulating subsystem 334 may transmit circuit status information to the controller 322 over the lines 360. Each output is connected to one of the leads 130, thereby stimulating a single one of the electrodes 142 in the electrode array 140.

In the embodiment illustrated, the stimulating subsystem 334 includes a digital-to-analog amplifier 362 that receives stimulating waveform shape information from the controller 322. The amplifier 362 turn drives (voltage or current) amplifiers 364. The outputs of the amplifiers 364 are monitored and potentially limited by over-voltage or over-current protection circuitry 366).

The muscle stimulator drive 336 is configured to drive one or more of the muscle electrodes 312. Alternatively, the muscle stimulator drive 336 may provide an interface to a separate drive system (not shown). The muscle stimulator drive 336 is connected by bidirectional control lines 368 to the controller 322 to control the operation of the muscle stimulator drive 336.

The sensor interface 338 interfaces with one or more of the sensors 188 (the EMG sensors 190, joint angle sensors 191, accelerometers 192, and the like). Depending upon the implementation details, the sensor interface 338 may include digital signal inputs (not shown), low noise amplifiers (not shown) configured for analog signal line inputs, and analog inputs (not shown) connected to A/D circuits (not shown).

The controller 322 may be connected wirelessly to the external programming unit 150 via the communication connection 155A. The communication connection 155A may be configured to provide bi-directional wireless communication over which the controller 322 may receive system control commands and data from the external programming unit 150, as well as transmit status information and data to the external programming unit 150. In some embodiments, the communication connection 155A may include one or more analog communication channels, one or more digital communication channels, or a combination thereof.

The RF power interface 342 may receive power wirelessly from the external programming unit 150 via the power transfer connection 155B. The RF power interface 342 may include a radio frequency ("RF") charging coil 372. In such embodiments, the RF charging coil 284 of the external wireless power circuit 280 may be configured to transfer power (e.g., inductively) to the RF charging coil 272. Optionally, communication channels may be multiplexed on the wireless transmission.

The power source 344 may be implemented using one or more rechargeable multi-cell Lithium Ion Polymer batteries.

Third Embodiment

Figure 11:
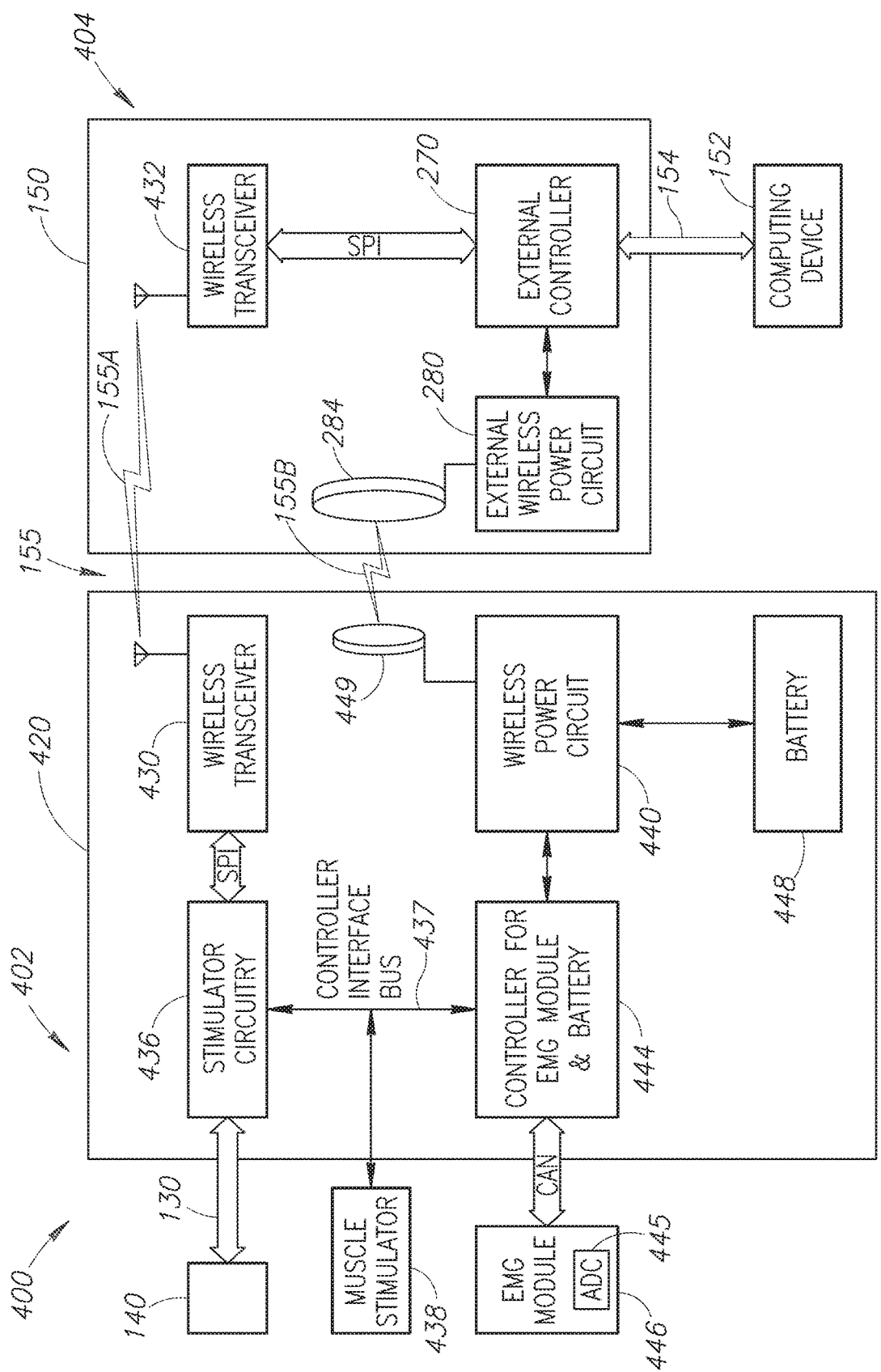
FIG. 11 is a block diagram of a third embodiment of an implantable assembly and the external system.

FIG. 11 is a block diagram of a first embodiment of a system 400. The system 400 includes an implantable assembly 402 substantially similar to the assembly 100 described above, and an external system 404 substantially similar to the external system 180 described above. Therefore, only components of the assembly 402 that differ from those of the assembly 100, and components of the external system 404 that differ from those of the external system 180 will be described in detail. For ease of illustration, like reference numerals have been used to identify like components in FIGS. 1-3, 5, and 10-12B.

The assembly 402 includes a neurostimulator device 420, the electrode array 140, and the one or more traces 130. The neurostimulator device 420 is connected by a controller interface bus 437 to an implantable muscle stimulator package 438, and an EMG module 446. The neurostimulator device 420 is configured to interface with and control both the implantable muscle stimulator package 438 and the EMG module 446. By way of a non-limiting example, suitable implantable muscle stimulator packages for use with the system may include a Networked Stimulation system developed at Case Western University.

The neurostimulator device 420 includes a transceiver 430, stimulator circuitry 436, a wireless power circuit 440, a power source 448 (e.g., a battery), and a controller 444 for the EMG module 446 and the power source 448. The neurostimulator device 420 illustrated is configured interface with and control the separate EMG module 446. However, in alternate embodiments, EMG recording and management capabilities may be incorporated into the neurostimulator device 420, as they are in the neurostimulator device 320 (see FIG. 10). In the embodiment illustrated, the EMG module 446 includes an analog to digital converter ("ADC") 445. Digital data output by the EMG module 446 and received by the controller 444 is sent to the stimulator circuitry 436 via the controller interface bus 437.

The transceiver 430 is configured to communicate with a corresponding transceiver 432 of the external programming unit 150 connected to the external controller 270 over the communication connection 155A. The transceivers 430 and 432 may each be implemented as Medical Implant Communication Service ("MICS") band transceivers. By way of a non-limiting example, the transceiver 432 may be implemented using ZL70102 MICS band transceiver connected to a 2.45 GHz transmitter. The transmitter may be configured to "wake up" the transceiver 430. By way of a non-limiting example, the transceiver 430 may be implemented using a ZL70102 MICS band transceiver.

Figure 12A:
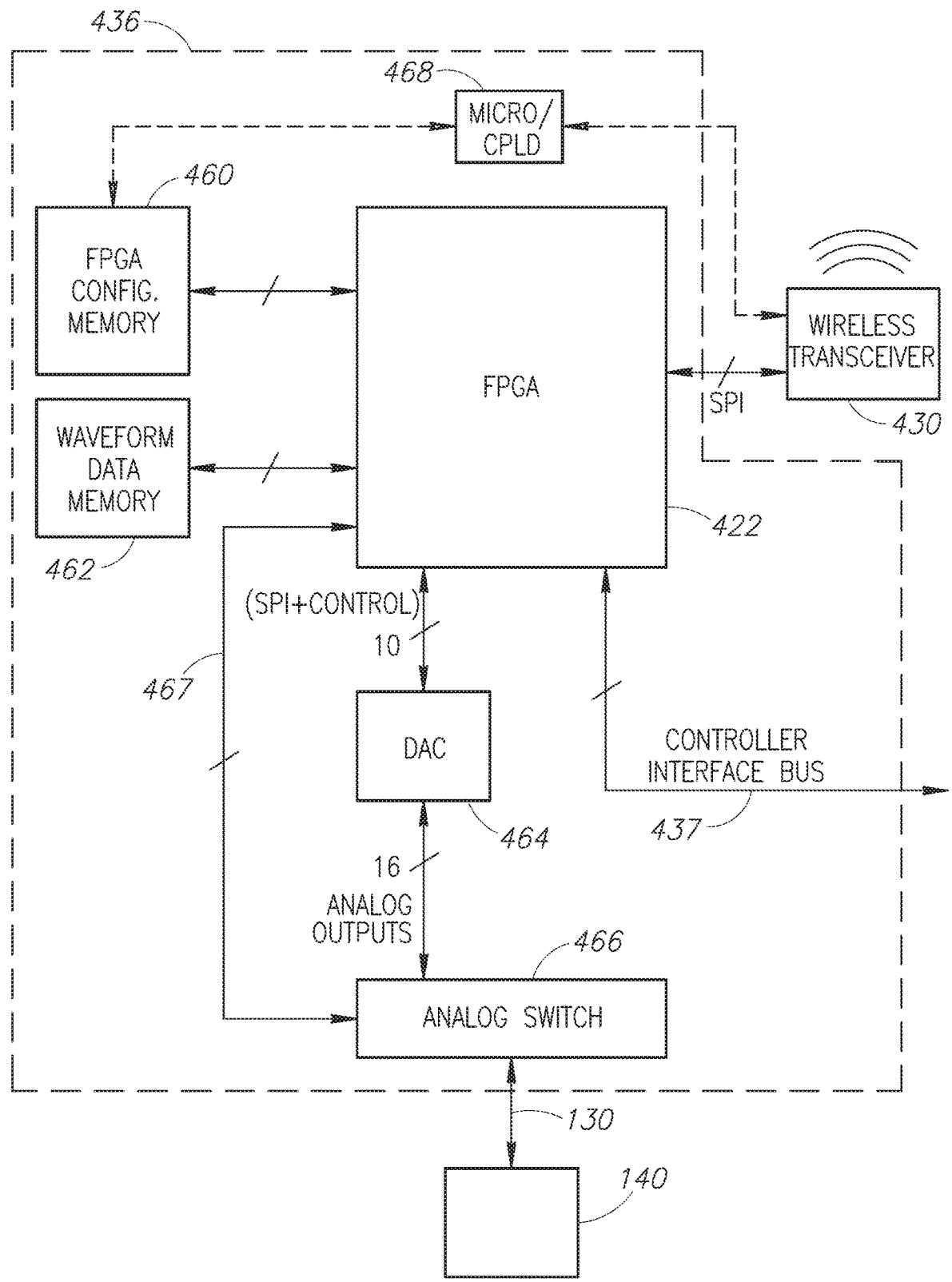
FIG. 12A is a block diagram of stimulator circuitry and a wireless transceiver of a neurostimulator device of the implantable assembly of FIG. 11.
Figure 12B:
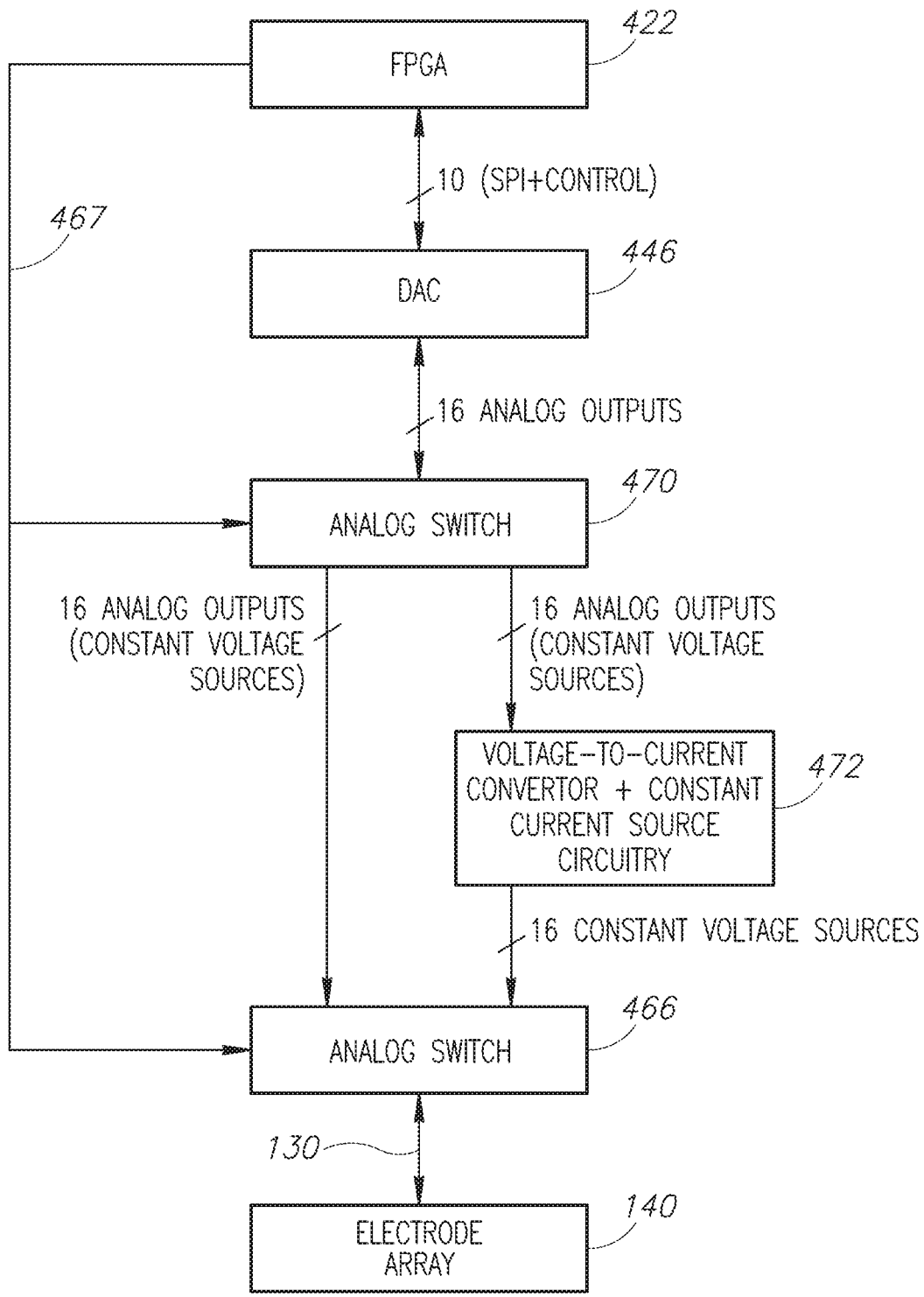
FIG. 12B is a block diagram of an alternate embodiment of the stimulator circuitry of FIG. 12A.

FIG. 12A is a block diagram illustrating the transceiver 430 and the components of the stimulator circuitry 436. In FIG. 12A, connections labeled "SPI" have been implemented for illustrative purposes using Serial Peripheral Interface Buses.

Referring to FIG. 12A, the stimulator circuitry 436 includes a central processing unit ("CPU") or controller 422, one or more data storage devices 460 and 462, a digital to analog converter 464, an analog switch 466, and an optional complex programmable logic device ("CPLD") 468. In the embodiment illustrated, the controller 422 has been implemented using a field-programmable gate array ("FPGA"). Digital data output by the EMG module 446 and received by the controller 444 is sent to the controller 422 via the controller interface bus 437.

The storage device 460 is connected to the controller 422 and configured to store instructions for the controller 422. By way of a non-limiting example, the storage device 460 may be implemented as FPGA configured memory (e.g., PROM or non-flash memory). The optional CPLD 468 is connected between the transceiver 430 and the storage device 460. The optional CPLD 468 may be configured to provide robust access to the storage device 460 that may be useful for storing updates to the instructions stored on the storage device 460.

The storage device 462 is connected to the controller 422 and configured to store recorded waveform data. By way of a non-limiting example, the storage device 462 may include 8 MB or more of memory.

The digital to analog converter 464 is connected to the controller 422 and configured to convert digital signals received therefrom into analog signals to be delivered to the electrode array 140. The digital to analog converter 464 may be implemented using an AD5360 digital to analog converter.

The analog switch 466 is positioned between the digital to analog converter 464 and the leads 130. The analog switch 466 is configured to modulate (e.g., selectively switch on and off) the analog signals received from the digital to analog converter 464 based on instructions received from the controller 422. The analog switch 466 may include a plurality of analog switches (e.g., a separate analog switch for each channel). Optionally, the analog switch 466 may have a high-impedance mode. The analog switch 466 may be configured to operate in the high-impedance mode (in response to instructions from the controller 422 instructing the analog switch 466 to operate in the high-impedance mode) when the neurostimulator device is not delivering stimulation to the electrodes 142. The analog switch 466 may receive instructions from the controller 422 over one or more control lines 467.

In the embodiment illustrated, the ability to directly stimulate muscles (as an adjunct to the neurological stimulation) is not integrated into the neurostimulator device 420 as it is in the neurostimulator device 320 described above and illustrated in FIG. 10. Instead, the controller 422 communicates with the separate implantable muscle stimulator package 438 via the controller interface bus 437. Optionally, a monitor and control subsystem (like the monitor and control subsystem 332 of the neurostimulator device 320) may be omitted from the neurostimulator device 420. However, this is not a requirement.

The neurostimulator device 420 is configured to deliver stimulation to each of a plurality of channels independently. As explained above, each channel corresponds to one of the electrodes 142. Stimulation delivered over a channel is applied to the corresponding one of the electrodes 142. In the embodiment illustrated, the plurality of channels includes 16 channels. However, this is not a requirement. To deliver stimulation, the neurostimulator device 420 uses one positive channel and one negative channel.

In some embodiments, signals detected or received by one or more of the electrodes 142 may be received by the neurostimulator device 420 over the corresponding channels.

The neurostimulator device 420 may be configured to control the polarity (positive or negative) or tristate (positive, negative, or high Z) of each of the channels. The neurostimulator device 420 may be configured to deliver stimulation having a frequency within a range of about 0.1 Hz to about 100 Hz. The stimulation delivered may have an amplitude of about −10 Vdc to about +10 Vdc with an increment of about 0.1 Vdc. The neurostimulator device 420 is configured to generate stimulation having a standard waveform shape (e.g., sine, triangle, square, and the like) and/or a custom defined waveform shape. The duty cycle of the neurostimulator device 420 may be configured (for example, for square waveform shapes). The neurostimulator device 420 may provide phase shift in specified increments (e.g., in 25 microsecond increments).

The neurostimulator device 420 may be configured to satisfy timing requirements. For example, the neurostimulator device 420 may be configured to deliver a minimum pulse width of about 50 μs and to update all positive channels within a minimum pulse width. In such embodiments, a maximum number of positive channels may be determined (e.g., 15 channels). The neurostimulator device 420 may be configured to accommodate a minimum amount of phase shift (e.g., 25 μs phase shift). Further, the neurostimulator device 420 may be configured to update some channels during a first time period (e.g., 25 μs) and to rest during a second time period (e.g., 25 μs). The neurostimulator device 420 may be configured to simultaneously update the output channels.

The neurostimulator device 420 may be configured to satisfy particular control requirements. For example, it may be useful to configure the neurostimulator device 420 so that channel output configuration can be configured on the fly. Similarly, in some embodiments, practical limitations (e.g., a limit of a few seconds) may be placed on update time. Further, in some embodiments, the neurostimulator device 420 is configured to operate with adjustable custom waveform definitions. It may also be desirable to configure the neurostimulator device 420 such that output stimulation does not stop (or drop-out) during output reconfiguration.

In the embodiment illustrated in FIG. 12A, recording via the EMG module 446 (see FIG. 11) and delivering stimulation to the electrodes 142 may be performed completely separately (or independently). Further, in some embodiments, commands or instructions may be sent to the implantable muscle stimulator package 438 (or an integrated muscle stimulator system) independently or separately. Thus, this embodiment may operate in a full duplex mode.

In an alternate embodiment, the neurostimulator device 420 may be connected to the EMG sensors 190 or recording electrodes (not shown) that are independent of the electrodes 142 used to deliver stimulation. In such embodiments, a pre-amp (not shown) and ADC (not shown) may be included in the stimulator circuitry 436 and used to send digital EMG or nerve recording signals directly to the controller 422. Such embodiments provide two completely separate, continuous time channels between recording and stimulation and therefore, may be characterized as being operable in a full duplex mode. Optionally, the recording electrodes may be incorporated in the electrode array 140 and/or a separate electrode array (not shown).

In another alternate embodiment, the analog switch 466 may be used to switch between a stimulate mode and a record mode. The analog switch 466 may receive instructions from the controller 422 (via the control lines 467) instructing the analog switch 466 in which mode to operate. This implementation may help reduce the number of electrodes by using the same electrodes or a subset thereof to record and stimulate. This exemplary embodiment may be characterized as being operable in a half-duplex mode.

The embodiment illustrated in FIG. 12A the stimulator circuitry 436 is configured to operate in a constant voltage mode. Thus, the output of the DAC 446 (and the analog switch 466) is a plurality (e.g., 16) of constant voltage signals (or sources). However, referring to FIG. 12B, in alternate embodiments, the stimulator circuitry 436 is configured to switch between the constant voltage mode and a constant current mode. In this embodiment, the analog switch 466 includes a separate analog switch (e.g., a single pull, double throw switch) for each channel and a 2-1 multiplexer ("MUX"). This embodiment also includes an analog switch 470 and a circuit block 472. The analog switch 470 may include a separate analog switch (e.g., a single pull, double throw switch) for each channel and a 1-2 demultiplexer ("DEMUX"). The output of the analog switch 470 is a plurality (e.g., 16) of constant voltage signals selectively delivered to either the analog switch 466 or the circuit block 472. Essentially, the analog switches 470 and 466 may be configured to allow either a constant current signal or constant voltage signal to be applied to the electrode array 140.

The circuit block 472 includes voltage to current converter circuitry and constant current source circuitry. The circuit block 472 receives the plurality (e.g., 16) of constant voltage signals from the analog switch 470 and outputs a plurality (e.g., 16) of constant current signals (or sources).

The neurostimulator device 420 may be configured to provide feedback (received from the sensor 188, recording electrodes, and/or the electrodes 142) to the controller 422, which the controller may use to modify or adjust the stimulation pattern or waveform. In embodiments in which the controller 422 is implemented using a FPGA, the FPGA may be configured to modify the complex stimulation patterns delivered to the subject 102 in near real-time. Further, the controller 422 may be used to customize the complex stimulation pattern(s) for different subjects.

The wireless power circuit 440 illustrated include a RF charging coil 449 configured to receive power via the power transfer connection 1556. The power received may be used to charge the power source 448 (e.g., a battery).

Machine Learning Method

Since each patient's injury or illness is different, it is believed the best pattern of stimulation will vary significantly across patients. Furthermore, it is believed optimal stimuli will change over time due to the plasticity of the spinal cord 110. For this purpose, a learning system (e.g., the computing device 152 and/or one of the neurostimulator devices 220, 320, and 420) may be programmed to "learn" a personalized (or custom) stimuli pattern for the subject 102, and continually adapt this stimuli pattern over time.

The learning system receives input from one or more of the sensors 188 and/or external adjunctive devices, which may be implanted along with the neurostimulator device 220, 320, or 420 and/or temporarily applied to the subject 102 (e.g., in a clinical setting). Examples of such sensors include the EMG sensors 190, joint angle sensors 191, accelerometers 192, and the like. The external adjunctive devices may include support platforms, support stands, external bracing systems (e.g., exo-skeletal systems), in shoe sensor systems, and/or therapy machines. Information received from the electrodes 142, the connections 194, and/or the external adjunctive devices may be used to tune and/or adjust the complex stimulation pattern delivered by the neurostimulator devices 220, 320, and 420.

The learning system may perform a machine learning method (described below) that determines suitable or optimal stimulation parameters based on information received from the sensors 188. It is believed that it may be more efficient to perform larger adjustments to the stimulation in a clinical setting (e.g., using the computing device 152 and external programming unit 150), and smaller adjustments (fine tuning) on an ongoing basis (e.g., using one of the neurostimulator devices 220, 320, and 420).

In the clinical setting, numerous and sensitive EMG sensors 190, as well as foot pressure sensors (not shown), accelerometers 192, and motion tracking systems (not shown) can be used to gather extensive data on the performance of the subject 102 in response to specific stimuli. These assessments of performance can be used by the learning system to determine suitable and/or optimal stimulation parameters. Soon after the subject 102 is implanted with one of the neurostimulator devices 220, 320, and 420, the subject 102 will begin physical training in a clinical setting (e.g., walking on the treadmill 170), which will continue for a few months during which the learning system can tune the stimulation parameters. Thereafter, the subject 102 may return to the clinic occasionally (e.g., on a regular basis (e.g., every 3 months)) for more major "tune ups."

As mentioned above, outside the clinic, the neurostimulator devices 220, 320, and 420 receive signals from on-board, implanted, and external sensing systems (e.g., the electrodes 142, the sensors 188, and the like). This information may be used by the one of the neurostimulator devices 220, 320, and 420 to tune the stimulation parameters.

As mentioned above, the neurostimulator devices 220, 320, and 420 may each be configured to provide patient-customized stimuli, compensate for errors in surgical placement of the electrode array 140, and adapt the stimuli over time to spinal plasticity (changes in spinal cord function and connectivity). However, with this flexibility comes the burden of finding suitable stimulation parameters (e.g., a pattern of electrode array stimulating voltage amplitudes, stimulating currents, stimulating frequencies, and stimulating waveform shapes) within the vast space of possible patterns and parameters. It is impractical to test all possible parameters within this space to find suitable and/or optimal parameter combinations. Such a process would consume a large amount of clinical resources, and may also frustrate the subject 102. Therefore, a machine learning method is employed to more efficiently search for effective parameter combinations. Over time, the machine learning method may be used to adapt (e.g., occasionally, periodically, continually, randomly, as needed, etc.) the operating parameters used to configure the stimulation.

The machine learning method (which seeks to optimize the stimuli parameters) alternates between an exploration phase (in which the parameter space is searched and a regression model built that relates stimulus and motor response) and an exploitation phase (in which the stimuli patterns are optimized based on the regression model). As is apparent to those of ordinary skill in the art, many machine learning methods incorporate exploration and exploitation phases and such methods may be adapted to determine suitable or optimal stimulation parameters through application of ordinary skill in the art to the present teachings.

By way of a non-limiting example, a *Gaussian Process Optimization* ("GPO") may be used to determine the stimulation parameters. C. E. Rasmussen, *Gaussian Processes for Machine Learning*, MIT Press, 2006. GPO is an active learning method with an update rule that explores and exploits the space of possible stimulus parameters while constructing an online regression model of the underlying mapping from stimuli to motor performance (e.g., stepping, standing, arm reaching, and the like). Gaussian Process Regression ("GPR"), the regression modeling technique at the core of GPO, is well suited to online use because it requires fairly minimal computation to incorporate each new data point, rather than the extensive re-computation of many other machine learning regression techniques. GPR is also non-parametric; predictions from GPO are based on an ensemble of an infinite number of models lying within a restricted set, rather than from a single model, allowing it to avoid the over-fitting difficulties inherent in many parametric regression and machine learning methods.

GPR is formulated around a kernel function, $k(\cdot,\cdot)$, which can incorporate prior knowledge about the local shape of the performance function (obtained from experience and data derived in previous epidural stimulation studies), to extend inference from previously explored stimulus patterns to new untested stimuli. Given a function that measures performance (e.g., stepping, standing, or reaching), GPO is based on two key formulae and the selection of an appropriate kernel function. The core GPO equation describes the predicted mean $\mu_t(x^*)$ and variance $\sigma_t^2(x^*)$ of the performance function (over the space of possible stimuli), at candidate stimuli $x^*$, on the basis of past measurements (tests of stimuli values $X=\{x_1, x_2, \ldots\}$ that returned noisy performance values $Y_t=\{y_1, y_2, \ldots\}$)

$$\mu_t(x^*)=k(x^*,X)[K_t(X,X)+\sigma_n^2 I]^{-1} Y_t;$$

$$\sigma_t^2(x^*)=k(x^*,x^*)-k(x^*,X)[K_t(X,X)+\sigma_n^2 I]^{-1} k(X,x^*)$$

where $K_t$ is the noiseless covariance matrix of past data, and $\sigma_n^2$ is the estimated noise covariance of the data that is used in the performance evaluation. To balance exploration of regions of the stimuli space where little is known about expected performance with exploitation of regions where we expect good performance, GPO uses an upper confidence bound update rule (N. Srinivas, A. Krause, et. al., "Guassian Process Optimization in the bandit setting: No Regret and Experimental Design," *Proc. Conf. on Machine Learning*, Haifa Israel, 2010.):

$$x_{t+1}=\mathrm{argmax}_{x \in x^*}[\mu_t(x)+\beta_t \sigma_t(x)]. \quad (1)$$

When the parameter $\beta_t$ increases with time, and if the performance function is a Gaussian process or has a low Reproducing Kernel Hilbert Space norm relative to a Gaussian process, GPO converges with high probability to the optimal action, given sufficient time.

The method described above is a sequential updating method that works in a simple cycle. A single known stimulus is applied to the electrode array, and the patient's response to the stimulus is measured using either implanted sensors (such as EMG sensors 190 connected to the connections 194), and/or using external sensors (such as surface EMG electrodes, foot plate forces, and motion capture data gathered from a video monitoring system). The mean and covariance of the Gaussian Process system are immediately updated based on the single stimulus, and the upper confidence procedure of Equation (1) selects the next stimuli pattern to evaluate. This process continues until a termination criteria, such as a minimal increase in performance, is reached.

Alternatively, it may be desirable to propose a batch of stimuli to apply in one clinical therapy session and then evaluate the batch of results, updating the regression model using the entire batch of stimulus-response pairs, and then proposing a new batch of stimulus patterns to be evaluated during the next clinical session. The upper confidence bound method described above can be readily extended to this case. T. Desautels, J. Burdick, and A. Krause, "Parallelizing Exploration-Exploitation Tradeoffs with Gaussian Process Bandit Optimization," (submitted) *International Conference on Machine Learning*, Edinburgh, Scotland, Jun. 26-Jul. 1, 2012. The stimulus update rule for the batch process can take the following form:

$$x_{t+1} = \text{argmax}_{x \in X^*}[\mu_{t-B}(x) + \mu_t \sigma_t(x)]. \quad (2)$$

where now the Equation (2) is evaluated B times to produce a batch of B proposed stimuli to evaluate, but the mean function $\mu(x)$ is only updated at the end of the last batch of experiments, and the variance $\sigma_t(x)$ is updated for each item in the proposed batch.

The definition of a performance function that characterizes human motor behavior (e.g. standing or stepping behavior) may depend upon at least two factors: (1) what kinds of motor performance data is available (e.g., video-based motion capture data, foot pressure distributions, accelerometers, EMG measurements, etc.); and (2) the ability to quantify motor performance. While more sensory data is preferable, a machine learning approach to parameter optimization can employ various types of sensory data related to motor performance. It should be noted that even experts have great difficulty determining stepping or standing quality from such data without also looking at video or the actual subject 102 as he/she undertakes a motor task. However, given a sufficient number of training examples from past experiments and human grading of the standing or stepping in those experiments, a set of features that characterize performance (with respect to the given set of available sensors) can be learned and then used to construct a reasonable performance model that captures expert knowledge and uses the available measurement data.

FIG. 13 depicts a multi-compartment physical model of the electrical properties of a mammalian spinal cord 500, along with a 27 electrode implementation of the electrode array 140 placed in an epidural position. In FIG. 1, first and second electrodes 502 and 504 have been activated (i.e., are delivering stimulation to the spinal cord 500). One of the activated electrodes is the cathode and the other the anode. Electrode 506 has not been activated and is considered to be neutral. In FIG. 14, the electrodes 502 and 504 have been activated. FIG. 14 shows the isopotential contours 508 (in slice through the center of the bipolarly activated electrodes) of the stimulating electric field for the 2-electrode stimulation example. The mammalian spinal cord 500 includes a dura 510, white matter 512, gray matter 514, and epidural fat 516.

FIG. 15 shows the instantaneous regret (a measure of the error in the machine learning methods search for optimal stimuli parameters) when the Gaussian Process Optimization method summarized above is used to optimize the array stimulus pattern that excites neurons in the dorsal roots between segments L2 and S2 in the simulated spinal cord 500. The instantaneous regret performance shows that the machine learning method rapidly finds better stimulating parameters, but also continually explores the stimulation space (the "bursts" in the graph of instantaneous regret correspond to excursions of the machine learning method to regions of stimulus parameter space which were previously unknown, but which have been found to have poor performance).

FIG. 16 shows the average cumulative regret vs. learning iteration. The average cumulative regret is a smoothed version of the regret performance function that better shows the machine learning method's overall progress in selecting optimal stimulation parameters.

The machine learning method may be performed by the computing device 152 and/or one of the neurostimulator devices 220, 320, and 420. Thus, instructions for performing the method may be stored in a non-transitory memory storage hardware device of at least one of the computing device 152, the neurostimulator device 220, the neurostimulator device 320, and the neurostimulator device 420. Further, these devices may interact during the performance of the method or distribute portions of its execution. By performing the method, the computing device 152, the neurostimulator device 220, the neurostimulator device 320, and/or the neurostimulator device 420 may determine the stimulation parameters (e.g., the waveform shape, amplitude, frequency, and relative phasing) of the complex stimulation pattern applied to the electrodes 142. As discussed above, the machine learning method may implement a Sequential or Batch Gaussian Process Optimization ("GPO") method using an Upper Confidence Bound procedure to select and optimize the stimulation parameters.

Computing Device

FIG. 17 is a diagram of hardware and an operating environment in conjunction with which implementations of the computing device 152 and/or the remote computing device 157 may be practiced. The description of FIG. 17 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that implementations may be practiced with other computer system configurations, including hand-held devices, multiprocessor systems, microprocessor-based or programmable consumer electronics, network PCs, minicomputers, mainframe computers, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 17 includes a general-purpose computing device in the form of a computing device 12. The computing device 152 and/or the remote computing device 157 may be substantially identical to the computing device 12. The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like.

The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types of physical feedback (e.g., a force feed back game controller).

The input devices described above are operable to receive user input and selections. Together the input and display devices may be described as providing a user interface.

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 17 include a local-area network (LAN) 51 and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

In some embodiments, the system memory 22 stores computer executable instructions that when executed by one or more processors cause the one or more processors to perform all or portions of the machine learning method described above. Such instructions may be stored on one or more non-transitory computer-readable media (e.g., the storage device 460 illustrated in FIG. 12A).

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

We claim:

1. A neurostimulator device comprising:
    a stimulation assembly connectable to a plurality of electrodes, wherein the plurality of electrodes are configured to stimulate a spinal cord using an applied complex stimulation pattern;
    an interface configured to receive movement data indicative of a response related to stimulation of the spinal cord; and
    a processor configured to modify the applied complex stimulation pattern to create a modified complex stimulation pattern for subsequent stimulation of the spinal cord by
        processing the movement data, and
        performing an optimization algorithm that includes a predicted mean and a variance of a motor performance function for a plurality of candidate complex stimulation patterns, including the applied complex stimulation pattern, based on at least on one of (i) previous movement data including the received movement data, and (ii) stimulation study movement data that is derived from a stimulation study,
    wherein the optimization algorithm includes an upper confidence bound rule for applying a weight for modifying the applied complex stimulation pattern based on a number of times movement data is received regarding stimulation of the spinal cord, and
    wherein the upper confidence bound rule causes the applied complex stimulation pattern to be modified through convergence of the optimization algorithm toward an optimal candidate complex stimulation pattern.

2. The neurostimulator device of claim 1, wherein the movement data includes at least one of motion data, metabolic data, or physiological data, and the interface is configured to receive the movement data from at least one of an electromyography sensor, an evoked potential sensor, a joint angle sensor, a flex sensor, an accelerometer, a gyroscope sensor, a flow sensor, a pressure sensor, a load sensor, a temperature sensor, or a combination thereof.

3. The neurostimulator device of claim 1, wherein the interface is configured to receive the movement data from at least one of a support platform, a support stand, an external bracing system, an in shoe sensor system, a therapy machine, or a combination thereof.

4. The neurostimulator device of claim 1, wherein the interface is configured to receive the movement data from at least one of a clinician computer, a remote computing device, a motion capture system, a video-based system, or a combination thereof.

5. The neurostimulator device of claim 1, wherein at least one of the movement data or the motor performance function is based on at least one of voluntary movement of muscles involved in standing, voluntary movement of muscles involved in stepping, voluntary movement of muscles involved in reaching, voluntary movement of muscles involved in grasping, voluntarily changing positions of one or both legs, voluntarily changing positions of one or both arms, voiding a bladder, sexual function, voiding a bowel, postural activity, locomotor activity, cardiovascular function, respiratory function, digestive function, autonomic function, motor function, vasomotor function, cognitive function, body temperature, metabolic processes, or a combination thereof.

6. The neurostimulator device of claim 1 configured to aid a patient having a neurologically derived paralysis in a portion of the patient's body affected by a lesion to the spinal cord, wherein the spinal cord includes at least one selected spinal circuit that has a first stimulation threshold representing a minimum amount of stimulation required to activate the at least one selected spinal circuit, and a second stimulation threshold representing an amount of stimulation above which the at least one selected spinal circuit is fully activated.

7. The neurostimulator device of claim 6, wherein at least one of the applied complex stimulation pattern, the modified complex stimulation pattern, or the plurality of candidate complex stimulation patterns, is below the second stimulation threshold such that the at least one selected spinal circuit is at least partially activatable by the addition of at least one of (a) neurological signals originating from the portion of the patient's body having the paralysis, and (b) supraspinal signals.

8. The neurostimulator device of claim 1, wherein at least one of the applied complex stimulation pattern, the modified complex stimulation pattern, or the plurality of candidate complex stimulation patterns is configured to stimulate the spinal cord and improve or restore voluntary movement, an autonomic function, a motor function, a metabolic function, or a combination thereof.

9. The neurostimulator device of claim 1, wherein the plurality of electrodes includes at least four groups of electrodes.

10. The neurostimulator device of claim 9, wherein at least one of the applied complex stimulation pattern or the modified complex stimulation pattern comprises different electrical stimulation for each of the groups of electrodes.

11. The neurostimulator device of claim 1, wherein one electrode of the plurality of electrodes is located at neural tissue and another electrode of the plurality of electrodes is located at an end organ.

12. A method of operating a neurostimulator device that includes a stimulation assembly connectable to a plurality of electrodes for stimulating a portion of a patient, the method comprising:
    applying a first complex stimulation pattern to the portion of the patient using the stimulation assembly;
    receiving, via an interface, response data that is related to stimulation of the portion of the patient; and
    modifying, via a processor, the first complex stimulation pattern to create a second complex stimulation pattern for subsequent stimulation of the portion of the patient by
        processing the response data, and
        performing an optimization algorithm that includes a predicted mean and a variance of a motor performance function for a plurality of candidate complex stimulation patterns, including the first complex stimulation pattern, based on at least on one of (i) previous response data including the received response data, and (ii) stimulation study response data that is derived from a stimulation study,
    wherein the optimization algorithm includes an upper confidence bound rule for applying a weight for modifying the first complex stimulation pattern based on a number of times response data is received regarding stimulation of the portion of the patient, and
    wherein the upper confidence bound rule modifies the first complex stimulation pattern through convergence of the optimization algorithm toward an optimal candidate complex stimulation pattern.

13. The method of claim 12, further comprising controlling, via the processor, a training device to subject the patient to physical training before or during application of at least one of the first complex stimulation pattern or the second complex stimulation pattern.

14. The method of claim 12, wherein the response data is recorded by at least one of an electromyography sensor, an evoked potential sensor, a joint angle sensor, a flex sensor, an accelerometer, a gyroscope sensor, a flow sensor, a pressure sensor, a load sensor, a temperature sensor, a support platform, a support stand, an external bracing system, an in shoe sensor system, a therapy machine, a clinician computer, a remote computing device, a motion capture system, a video-based system, or a combination thereof.

15. The method of claim 12, wherein stimulation of the portion of the patient is configured to improve or restore at least one of voluntary movement of muscles involved in standing, voluntary movement of muscles involved in stepping, voluntary movement of muscles involved in reaching, voluntary movement of muscles involved in grasping, voluntarily changing positions of one or both legs, voluntarily changing positions of one or both arms, voiding the patient's bladder, sexual function, voiding the patient's bowel, postural activity, locomotor activity, cardiovascular function, respiratory function, digestive function, autonomic function, motor function, vasomotor function, cognitive function, body temperature, metabolic processes, or a combination thereof.

16. The method of claim 12, wherein at least one of the first complex stimulation pattern, the second complex stimulation pattern, or the plurality of candidate complex stimulation patterns is below a stimulation threshold such that the portion of the patient is at least partially activatable by addition of at least one of (a) neurological signals originating from the portion of the patient's body having the paralysis, and (b) supraspinal signals.

17. The method of claim 12, further comprising applying an adjustment to the second complex stimulation pattern provided by a clinician.

18. The method of claim 12, wherein at least one of the first complex stimulation pattern, the second complex stimulation pattern, or the plurality of candidate complex stimulation patterns includes a stimulation parameter specifying at least one of a waveform shape, an amplitude, a waveform period, or a waveform frequency.

19. The method of claim 12, wherein at least one of the first complex stimulation pattern, the second complex stimulation pattern, or the plurality of candidate complex stimulation patterns includes a stimulation timing that indicates that stimulation is to be applied to each of the plurality of electrodes.

20. The method of claim 12, wherein at least one of the first complex stimulation pattern, the second complex stimulation pattern, or the plurality of candidate complex stimulation patterns includes a transition parameter that specifies how a respective pattern is adapted over time to transition to another pattern.

* * * * *